US011261236B2

(12) United States Patent
Kim et al.

(10) Patent No.: US 11,261,236 B2
(45) Date of Patent: Mar. 1, 2022

(54) FUSION PEPTIDE COMPRISING THROMBUS-TARGETING PEPTIDE, FERRITIN FRAGMENT AND THROMBOLYTIC PEPTIDE, AND USE THEREOF

(71) Applicant: Kyungpook National University Industry-Academic Cooperation Foundation, Daegu (KR)

(72) Inventors: Soyoun Kim, Daegu (KR); Jun Young Seo, Daegu (KR); In San Kim, Seoul (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 56 days.

(21) Appl. No.: 16/475,955

(22) PCT Filed: Jan. 4, 2018

(86) PCT No.: PCT/KR2018/000174
§ 371 (c)(1),
(2) Date: Sep. 10, 2019

(87) PCT Pub. No.: WO2018/128412
PCT Pub. Date: Jul. 12, 2018

(65) Prior Publication Data
US 2019/0389936 A1    Dec. 26, 2019

(30) Foreign Application Priority Data

Jan. 6, 2017  (KR) ................. 10-2017-0002588
Dec. 28, 2017  (KR) ................. 10-2017-0183222

(51) Int. Cl.
| C07K 14/79 | (2006.01) |
| A61K 47/66 | (2017.01) |
| C07K 7/06 | (2006.01) |
| C07K 14/745 | (2006.01) |
| C12N 9/68 | (2006.01) |
| A61K 38/00 | (2006.01) |

(52) U.S. Cl.
CPC .............. *C07K 14/79* (2013.01); *A61K 47/66* (2017.08); *C07K 7/06* (2013.01); *C07K 14/745* (2013.01); *C12N 9/6435* (2013.01); *C12Y 304/21007* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 7,097,841 B2 | 8/2006 | Carter et al. |
| 2014/0377184 A1* | 12/2014 | Ruoslahti ................. C07K 7/06 424/9.6 |
| 2016/0038409 A1 | 2/2016 | Pan et al. |

FOREIGN PATENT DOCUMENTS

| KR | 101477123 B1 | 12/2014 |
| WO | 2016022547 A1 | 2/2016 |

OTHER PUBLICATIONS

Kim et al. "Double-Chambered Ferritin Platform: Dual-Function Payloads of Cytotoxic Peptides and Fluorescent Protein," Biomacromolecules 2016, 17, 12-19, published Dec. 9, 2015 (Year: 2015).*
Pilch et al. "Peptides selected for binding to clotted plasma accumulate in tumor stroma and wounds," PNAS 2006, 103, 2800-2804 (Year: 2006).*
Thijs et al. "Randomized, Placebo-Controlled, Dose-Ranging Clinical Trial of Intravenous Microplasmin in Patients With Acute Ischemic Stroke," Stroke 2009, 40, 3789-3795 (Year: 2009).*
Lapchak et al. "Microplasmin: A Novel Thrombolytic That Improves Behavioral Outcome After Embolic Strokes in Rabbits," Stroke 2002, 33, 2279-284 (Year: 2002).*
NCBI Reference Sequence: NP_000292.1, downloaded Jul. 12, 2021 (Year: 2021).*
Kim et al. "Double-chambered Ferritin Platform: Dual-function Payloads of Cytotoxic Peptides and Fluorescent Protein", Biomacromolecules, Dec. 9, 2015, vol. 17, pp. 12-19.
McCarthy et al., "Multifunctional nanoagent for thrombus-targeted fibrinolytic therapy", Nanomedicine, Jul. 1, 2012, vol. 7, p. 1017-1028, Future Medicine Ltd., London, GB.

(Continued)

*Primary Examiner* — Christina Bradley
(74) *Attorney, Agent, or Firm* — Levenfeld Pearlstein, LLC

(57) ABSTRACT

The present invention relates to: a fusion peptide comprising a thrombus-targeting peptide, ferritin fragment and a thrombolytic peptide; and a use thereof and, more specifically, to: a fusion peptide in which a thrombus-targeting peptide, ferritin fragment and a thrombolytic peptide are sequentially linked; a composition for preventing or treating thrombotic disorders, containing the same as an active ingredient; a method for treating thrombotic disorders; and a therapeutic use. According to the present invention, CLT-sFt-µPn DCNC as a novel plasmin-based thrombolytic nanocage has: an effect of targeting a site at which thrombus is present; a low sensitivity to inhibitors present in the circulatory system; pharmacological activity strongly destroying both arterial and venous thrombi; and no side effects of bleeding, and thus can be very useful in developing an agent for preventing or treating thrombotic disorders.

12 Claims, 16 Drawing Sheets
(14 of 16 Drawing Sheet(s) Filed in Color)
Specification includes a Sequence Listing.

(56) References Cited

OTHER PUBLICATIONS

Seo et al., "A targeted ferritin-microplasmin based thrombolytic nanocage selectively dissolves blood clots", Nanomedicine, Nanotechnology, Biology and Medicine, Apr. 1, 2018, vol. 14, pp. 633-642, Elsevier, NL.
Nguyen, "Genome squencing of methanotrophic bacteria isolated from alkaline groundwater in Korea", Geneseq, May 12, 2011, Republic of Korea.
Aoki et al., "Phylogenetic, cytological and morphological comparisons of Oxalis subsect. Oxalis (Oxalidaceae) in East Asia", Geneseq, Jan. 30, 2014, Japan.

* cited by examiner

SEQUENCE LISTING

```
<160> NUMBER OF SEQ ID NOS: 46

<210> SEQ ID NO 1
<211> LENGTH: 10
<212> TYPE: PRT
<213> ORGANISM: Artificial Sequence
<220> FEATURE:
<223> OTHER INFORMATION: Clot targetting peptide 1

<400> SEQUENCE: 1

Cys Asn Ala Gly Glu Ser Ser Lys Asn Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Clot targetting peptide 2
```

<400> SEQUENCE: 2

Cys Gly Leu Ile Ile Gln Lys Asn Glu Cys
1               5                   10

<210> SEQ ID NO 3
<211> LENGTH: 157
<212> TYPE: PRT
<213> ORGANISM: Artificial Sequence
<220> FEATURE:
<223> OTHER INFORMATION: Human ferritin light chain fragment (short
      ferritin)

<400> SEQUENCE: 3

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45

Ser His Phe Phe Arg Glu Leu Ala Glu Glu Lys Arg Glu Gly Tyr Glu
    50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
        115                 120                 125

Phe Leu Glu Thr His Phe Leu Asp Glu Glu Val Lys Leu Ile Lys Lys
    130                 135                 140

Met Gly Asp His Leu Thr Asn Leu His Arg Leu Gly Gly
145                 150                 155

<210> SEQ ID NO 4
<211> LENGTH: 161
<212> TYPE: PRT
<213> ORGANISM: Artificial Sequence
<220> FEATURE:
<223> OTHER INFORMATION: Human ferritin heavy chain fragment (short
      ferritin)

<400> SEQUENCE: 4

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
            115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala

<210> SEQ ID NO 5
<211> LENGTH: 250
<212> TYPE: PRT
<213> ORGANISM: Artificial Sequence
<220> FEATURE:
<223> OTHER INFORMATION: Microplasminogen

<400> SEQUENCE: 5

Ala Ala Pro Ser Phe Asp Cys Gly Lys Pro Gln Val Glu Pro Lys Lys
1               5                   10                  15

Cys Pro Gly Arg Val Val Gly Gly Cys Val Ala His Pro His Ser Trp
            20                  25                  30

Pro Trp Gln Val Ser Leu Arg Thr Arg Phe Gly Met His Phe Cys Gly
        35                  40                  45

Gly Thr Leu Ile Ser Pro Glu Trp Val Leu Thr Ala Ala His Cys Leu
    50                  55                  60

Glu Lys Ser Pro Arg Pro Ser Ser Tyr Lys Val Ile Leu Gly Ala His
65                  70                  75                  80

Gln Glu Val Asn Leu Glu Pro His Val Gln Glu Ile Glu Val Ser Arg
                85                  90                  95

Leu Phe Leu Glu Pro Thr Arg Lys Asp Ile Ala Leu Leu Lys Leu Ser
            100                 105                 110

Ser Pro Ala Val Ile Thr Asp Lys Val Ile Pro Ala Cys Leu Pro Ser
        115                 120                 125

Pro Asn Tyr Val Val Ala Asp Arg Thr Glu Cys Phe Ile Thr Gly Trp
    130                 135                 140

Gly Glu Thr Gln Gly Thr Phe Gly Ala Gly Leu Leu Lys Glu Ala Gln
145                 150                 155                 160

Leu Pro Val Ile Glu Asn Lys Val Cys Asn Arg Tyr Glu Phe Leu Asn
                165                 170                 175

Gly Arg Val Gln Ser Thr Glu Leu Cys Ala Gly His Leu Ala Gly Gly
            180                 185                 190

Thr Asp Ser Cys Gln Gly Asp Ser Gly Gly Pro Leu Val Cys Phe Glu
        195                 200                 205

Lys Asp Lys Tyr Ile Leu Gln Gly Val Thr Ser Trp Gly Leu Gly Cys
    210                 215                 220

Ala Arg Pro Asn Lys Pro Gly Val Tyr Val Arg Val Ser Arg Phe Val
225                 230                 235                 240

Thr Trp Ile Glu Gly Val Met Arg Asn Asn
                245                 250

<210> SEQ ID NO 6
<211> LENGTH: 230
<212> TYPE: PRT
<213> ORGANISM: Artificial Sequence
<220> FEATURE:
<223> OTHER INFORMATION: Microplasmin

<400> SEQUENCE: 6

Val Val Gly Gly Cys Val Ala His Pro His Ser Trp Pro Trp Gln Val
1               5                   10                  15

Ser Leu Arg Thr Arg Phe Gly Met His Phe Cys Gly Thr Leu Ile
            20                  25                  30

Ser Pro Glu Trp Val Leu Thr Ala Ala His Cys Leu Glu Lys Ser Pro
            35                  40                  45

Arg Pro Ser Ser Tyr Lys Val Ile Leu Gly Ala His Gln Glu Val Asn
50              55                  60

Leu Glu Pro His Val Gln Glu Ile Glu Val Ser Arg Leu Phe Leu Glu
65                  70                  75                  80

Pro Thr Arg Lys Asp Ile Ala Leu Leu Lys Leu Ser Ser Pro Ala Val
                85                  90                  95

Ile Thr Asp Lys Val Ile Pro Ala Cys Leu Pro Ser Pro Asn Tyr Val
                100                 105                 110

Val Ala Asp Arg Thr Glu Cys Phe Ile Thr Gly Trp Gly Glu Thr Gln
                115                 120                 125

Gly Thr Phe Gly Ala Gly Leu Leu Lys Glu Ala Gln Leu Pro Val Ile
            130                 135                 140

Glu Asn Lys Val Cys Asn Arg Tyr Glu Phe Leu Asn Gly Arg Val Gln
145                 150                 155                 160

Ser Thr Glu Leu Cys Ala Gly His Leu Ala Gly Gly Thr Asp Ser Cys
                165                 170                 175

Gln Gly Asp Ser Gly Gly Pro Leu Val Cys Phe Glu Lys Asp Lys Tyr
            180                 185                 190

Ile Leu Gln Gly Val Thr Ser Trp Gly Leu Gly Cys Ala Arg Pro Asn
            195                 200                 205

Lys Pro Gly Val Tyr Val Arg Val Ser Arg Phe Val Thr Trp Ile Glu
            210                 215                 220

Gly Val Met Arg Asn Asn
225                 230

<210> SEQ ID NO 7
<211> LENGTH: 445
<212> TYPE: PRT
<213> ORGANISM: Artificial Sequence
<220> FEATURE:
<223> OTHER INFORMATION: Fusion peptide full length

<400> SEQUENCE: 7

Met Gly Gly Thr Cys Asn Ala Gly Glu Ser Ser Lys Asn Cys Ala Ser
1               5                   10                  15

Gly His Met Ser Ser Gln Ile Arg Gln Asn Tyr Ser Thr Asp Val Glu
            20                  25                  30

Ala Ala Val Asn Ser Leu Val Asn Leu Tyr Leu Gln Ala Ser Tyr Thr
            35                  40                  45

Tyr Leu Ser Leu Gly Phe Tyr Phe Asp Arg Asp Asp Val Ala Leu Glu
50              55                  60

Gly Val Ser His Phe Phe Arg Glu Leu Ala Glu Lys Arg Glu Gly
65                  70                  75                  80

Tyr Glu Arg Leu Leu Lys Met Gln Asn Gln Arg Gly Gly Arg Ile Phe
            85                  90                  95

Leu Gln Asp Ile Lys Lys Pro Ala Glu Asp Glu Trp Gly Lys Thr Pro
                100                 105                 110

Asp Ala Met Lys Ala Ala Met Ala Leu Glu Lys Lys Leu Asn Gln Ala
                115                 120                 125

```
Leu Leu Asp Leu His Ala Leu Gly Ser Ala Arg Thr Asp Pro His Leu
    130                 135                 140

Cys Asp Phe Leu Glu Thr His Phe Leu Asp Glu Val Lys Leu Ile
145                 150                 155                 160

Lys Lys Met Gly Asp His Leu Thr Asn Leu His Arg Leu Gly Gly
                165                 170                 175

Ser Glu Phe Val Asp Gly Gly Ser Gly Thr Ser Ala Ala Pro Ser
            180                 185                 190

Phe Asp Cys Gly Lys Pro Gln Val Glu Pro Lys Lys Cys Pro Gly Arg
        195                 200                 205

Val Val Gly Gly Cys Val Ala His Pro His Ser Trp Pro Trp Gln Val
    210                 215                 220

Ser Leu Arg Thr Arg Phe Gly Met His Phe Cys Gly Gly Thr Leu Ile
225                 230                 235                 240

Ser Pro Glu Trp Val Leu Thr Ala Ala His Cys Leu Glu Lys Ser Pro
                245                 250                 255

Arg Pro Ser Ser Tyr Lys Val Ile Leu Gly Ala His Gln Glu Val Asn
            260                 265                 270

Leu Glu Pro His Val Gln Glu Ile Glu Val Ser Arg Leu Phe Leu Glu
        275                 280                 285

Pro Thr Arg Lys Asp Ile Ala Leu Leu Lys Leu Ser Ser Pro Ala Val
    290                 295                 300

Ile Thr Asp Lys Val Ile Pro Ala Cys Leu Pro Ser Pro Asn Tyr Val
305                 310                 315                 320

Val Ala Asp Arg Thr Glu Cys Phe Ile Thr Gly Trp Gly Glu Thr Gln
                325                 330                 335

Gly Thr Phe Gly Ala Gly Leu Leu Lys Glu Ala Gln Leu Pro Val Ile
            340                 345                 350

Glu Asn Lys Val Cys Asn Arg Tyr Glu Phe Leu Asn Gly Arg Val Gln
        355                 360                 365

Ser Thr Glu Leu Cys Ala Gly His Leu Ala Gly Gly Thr Asp Ser Cys
    370                 375                 380

Gln Gly Asp Ser Gly Gly Pro Leu Val Cys Phe Glu Lys Asp Lys Tyr
385                 390                 395                 400

Ile Leu Gln Gly Val Thr Ser Trp Gly Leu Gly Cys Ala Arg Pro Asn
                405                 410                 415

Lys Pro Gly Val Tyr Val Arg Val Ser Arg Phe Val Thr Trp Ile Glu
            420                 425                 430

Gly Val Met Arg Asn Asn Leu Glu His His His His
        435                 440                 445

<210> SEQ ID NO 8
<211> LENGTH: 175
<212> TYPE: PRT
<213> ORGANISM: Artificial Sequence
<220> FEATURE:
<223> OTHER INFORMATION: Human ferritin light chain

<400> SEQUENCE: 8

Met Ser Ser Gln Ile Arg Gln Asn Tyr Ser Thr Asp Val Glu Ala Ala
1               5                   10                  15

Val Asn Ser Leu Val Asn Leu Tyr Leu Gln Ala Ser Tyr Thr Tyr Leu
            20                  25                  30

Ser Leu Gly Phe Tyr Phe Asp Arg Asp Asp Val Ala Leu Glu Gly Val
        35                  40                  45
```

-continued

Ser His Phe Arg Glu Leu Ala Glu Glu Lys Arg Glu Gly Tyr Glu
50                  55                  60

Arg Leu Leu Lys Met Gln Asn Gln Arg Gly Gly Arg Ala Leu Phe Gln
65                  70                  75                  80

Asp Ile Lys Lys Pro Ala Glu Asp Glu Trp Gly Lys Thr Pro Asp Ala
                85                  90                  95

Met Lys Ala Ala Met Ala Leu Glu Lys Lys Leu Asn Gln Ala Leu Leu
            100                 105                 110

Asp Leu His Ala Leu Gly Ser Ala Arg Thr Asp Pro His Leu Cys Asp
                115                 120                 125

Phe Leu Glu Thr His Phe Leu Asp Glu Glu Val Lys Leu Ile Lys Lys
130                 135                 140

Met Gly Asp His Leu Thr Asn Leu His Arg Leu Gly Gly Pro Glu Ala
145                 150                 155                 160

Gly Leu Gly Glu Tyr Leu Phe Glu Arg Leu Thr Leu Lys His Asp
                165                 170                 175

<210> SEQ ID NO 9
<211> LENGTH: 183
<212> TYPE: PRT
<213> ORGANISM: Artificial Sequence
<220> FEATURE:
<223> OTHER INFORMATION: Human ferritin heavy chain

<400> SEQUENCE: 9

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
                20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
                115                 120                 125

His Leu Cys Asp Phe Ile Glu Thr His Tyr Leu Asn Glu Gln Val Lys
130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
                165                 170                 175

Gly Asp Ser Asp Asn Glu Ser
            180

<210> SEQ ID NO 10
<211> LENGTH: 9
<212> TYPE: PRT
<213> ORGANISM: Artificial Sequence
<220> FEATURE:
<223> OTHER INFORMATION: clot-targeting peptide example 1

<400> SEQUENCE: 10

```
Tyr Ile Gly Ser Arg Arg Gly Asp Ser
1               5
```

```
<210> SEQ ID NO 11
<211> LENGTH: 9
<212> TYPE: PRT
<213> ORGANISM: Artificial Sequence
<220> FEATURE:
<223> OTHER INFORMATION: clot-targeting peptide example 2

<400> SEQUENCE: 11

Tyr Ile Gly Ser Arg Arg Gly Asp Val
1               5
```

```
<210> SEQ ID NO 12
<211> LENGTH: 9
<212> TYPE: PRT
<213> ORGANISM: Artificial Sequence
<220> FEATURE:
<223> OTHER INFORMATION: clot-targeting peptide example 3

<400> SEQUENCE: 12

Tyr Ile Gly Ser Arg Arg Gly Asp Phe
1               5
```

```
<210> SEQ ID NO 13
<211> LENGTH: 10
<212> TYPE: PRT
<213> ORGANISM: Artificial Sequence
<220> FEATURE:
<223> OTHER INFORMATION: clot-targeting peptide example 4

<400> SEQUENCE: 13

Tyr Ile Gly Ser Arg Tyr Ile Gly Ser Lys
1               5                   10
```

```
<210> SEQ ID NO 14
<211> LENGTH: 10
<212> TYPE: PRT
<213> ORGANISM: Artificial Sequence
<220> FEATURE:
<223> OTHER INFORMATION: clot-targeting peptide example 5

<400> SEQUENCE: 14

Tyr Ile Gly Ser Arg Tyr Ile Gly Ser Arg
1               5                   10
```

```
<210> SEQ ID NO 15
<211> LENGTH: 9
<212> TYPE: PRT
<213> ORGANISM: Artificial Sequence
<220> FEATURE:
<223> OTHER INFORMATION: clot-targeting peptide example 6

<400> SEQUENCE: 15

Tyr Ile Gly Ser Lys Arg Gly Asp Ser
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: clot-targeting peptide example 7

<400> SEQUENCE: 16
```

```
Tyr Ile Gly Ser Lys Arg Gly Asp Phe
1               5

<210> SEQ ID NO 17
<211> LENGTH: 9
<212> TYPE: PRT
<213> ORGANISM: Artificial Sequence
<220> FEATURE:
<223> OTHER INFORMATION: clot-targeting peptide example 8

<400> SEQUENCE: 17

Tyr Ile Gly Ser Lys Arg Gly Asp Val
1               5

<210> SEQ ID NO 18
<211> LENGTH: 10
<212> TYPE: PRT
<213> ORGANISM: Artificial Sequence
<220> FEATURE:
<223> OTHER INFORMATION: clot-targeting peptide example 9

<400> SEQUENCE: 18

Tyr Ile Gly Ser Lys Tyr Ile Gly Ser Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: clot-targeting peptide example 10

<400> SEQUENCE: 19

Tyr Ile Gly Ser Lys Tyr Ile Gly Ser Arg
1               5                   10

<210> SEQ ID NO 20
<211> LENGTH: 8
<212> TYPE: PRT
<213> ORGANISM: Artificial Sequence
<220> FEATURE:
<223> OTHER INFORMATION: clot-targeting peptide example 11

<400> SEQUENCE: 20

Arg Gly Asp Ser Arg Gly Asp Ser
1               5

<210> SEQ ID NO 21
<211> LENGTH: 8
<212> TYPE: PRT
<213> ORGANISM: Artificial Sequence
<220> FEATURE:
<223> OTHER INFORMATION: clot-targeting peptide example 12

<400> SEQUENCE: 21

Arg Gly Asp Val Arg Gly Asp Val
1               5

<210> SEQ ID NO 22
<211> LENGTH: 8
<212> TYPE: PRT
<213> ORGANISM: Artificial Sequence
<220> FEATURE:
<223> OTHER INFORMATION: clot-targeting peptide example 13

<400> SEQUENCE: 22

Arg Gly Asp Phe Arg Gly Asp Phe
```

```
1               5

<210> SEQ ID NO 23
<211> LENGTH: 9
<212> TYPE: PRT
<213> ORGANISM: Artificial Sequence
<220> FEATURE:
<223> OTHER INFORMATION: clot-targeting peptide example 14

<400> SEQUENCE: 23

Arg Gly Asp Ser Tyr Ile Gly Ser Arg
1               5

<210> SEQ ID NO 24
<211> LENGTH: 9
<212> TYPE: PRT
<213> ORGANISM: Artificial Sequence
<220> FEATURE:
<223> OTHER INFORMATION: clot-targeting peptide example 15

<400> SEQUENCE: 24

Arg Gly Asp Ser Tyr Ile Gly Ser Lys
1               5

<210> SEQ ID NO 25
<211> LENGTH: 9
<212> TYPE: PRT
<213> ORGANISM: Artificial Sequence
<220> FEATURE:
<223> OTHER INFORMATION: clot-targeting peptide example 16

<400> SEQUENCE: 25

Arg Gly Asp Val Tyr Ile Gly Ser Arg
1               5

<210> SEQ ID NO 26
<211> LENGTH: 9
<212> TYPE: PRT
<213> ORGANISM: Artificial Sequence
<220> FEATURE:
<223> OTHER INFORMATION: clot-targeting peptide example 17

<400> SEQUENCE: 26

Arg Gly Asp Val Tyr Ile Gly Ser Lys
1               5

<210> SEQ ID NO 27
<211> LENGTH: 9
<212> TYPE: PRT
<213> ORGANISM: Artificial Sequence
<220> FEATURE:
<223> OTHER INFORMATION: clot-targeting peptide example 18

<400> SEQUENCE: 27

Arg Gly Asp Phe Tyr Ile Gly Ser Arg
1               5

<210> SEQ ID NO 28
<211> LENGTH: 9
<212> TYPE: PRT
<213> ORGANISM: Artificial Sequence
<220> FEATURE:
<223> OTHER INFORMATION: clot-targeting peptide example 19

<400> SEQUENCE: 28

Arg Gly Asp Phe Tyr Ile Gly Ser Lys
1               5
```

<210> SEQ ID NO 29
<211> LENGTH: 9
<212> TYPE: PRT
<213> ORGANISM: Artificial Sequence
<220> FEATURE:
<223> OTHER INFORMATION: clot-targeting peptide example 20

<400> SEQUENCE: 29

Cys Ser Asp Glu Asn Trp Leu Trp Cys
1               5

<210> SEQ ID NO 30
<211> LENGTH: 9
<212> TYPE: PRT
<213> ORGANISM: Artificial Sequence
<220> FEATURE:
<223> OTHER INFORMATION: clot-targeting peptide example 21

<400> SEQUENCE: 30

Cys Pro Met Ser Glu Trp Leu Tyr Cys
1               5

<210> SEQ ID NO 31
<211> LENGTH: 9
<212> TYPE: PRT
<213> ORGANISM: Artificial Sequence
<220> FEATURE:
<223> OTHER INFORMATION: clot-targeting peptide example 22

<400> SEQUENCE: 31

Cys Pro Trp Glu Ser Trp Thr Phe Cys
1               5

<210> SEQ ID NO 32
<211> LENGTH: 9
<212> TYPE: PRT
<213> ORGANISM: Artificial Sequence
<220> FEATURE:
<223> OTHER INFORMATION: clot-targeting peptide example 23

<400> SEQUENCE: 32

Cys Gln Glu Glu Pro Trp Leu Phe Cys
1               5

<210> SEQ ID NO 33
<211> LENGTH: 9
<212> TYPE: PRT
<213> ORGANISM: Artificial Sequence
<220> FEATURE:
<223> OTHER INFORMATION: clot-targeting peptide example 24

<400> SEQUENCE: 33

Cys Pro Gly Glu Asp Trp Leu Phe Cys
1               5

<210> SEQ ID NO 34
<211> LENGTH: 9
<212> TYPE: PRT
<213> ORGANISM: Artificial Sequence
<220> FEATURE:
<223> OTHER INFORMATION: clot-targeting peptide example 25

<400> SEQUENCE: 34

Cys Thr Gly Glu Pro Gly Pro Ile Cys
1               5

```
<210> SEQ ID NO 35
<211> LENGTH: 9
<212> TYPE: PRT
<213> ORGANISM: Artificial Sequence
<220> FEATURE:
<223> OTHER INFORMATION: clot-targeting peptide example 26

<400> SEQUENCE: 35

Cys Gln Leu Gly Tyr Arg Thr Tyr Cys
1               5

<210> SEQ ID NO 36
<211> LENGTH: 9
<212> TYPE: PRT
<213> ORGANISM: Artificial Sequence
<220> FEATURE:
<223> OTHER INFORMATION: clot-targeting peptide example 27

<400> SEQUENCE: 36

Cys Asp Gly Glu Pro Trp Leu Phe Cys
1               5

<210> SEQ ID NO 37
<211> LENGTH: 9
<212> TYPE: PRT
<213> ORGANISM: Artificial Sequence
<220> FEATURE:
<223> OTHER INFORMATION: clot-targeting peptide example 28

<400> SEQUENCE: 37

Cys Gly Trp Gly Ser Trp Lys Phe Cys
1               5

<210> SEQ ID NO 38
<211> LENGTH: 9
<212> TYPE: PRT
<213> ORGANISM: Artificial Sequence
<220> FEATURE:
<223> OTHER INFORMATION: clot-targeting peptide example 29

<400> SEQUENCE: 38

Cys Gly Trp Gly Ser Gly Lys Leu Cys
1               5

<210> SEQ ID NO 39
<211> LENGTH: 9
<212> TYPE: PRT
<213> ORGANISM: Artificial Sequence
<220> FEATURE:
<223> OTHER INFORMATION: clot-targeting peptide example 30

<400> SEQUENCE: 39

Cys Pro Gly Glu Pro Trp Thr Phe Cys
1               5

<210> SEQ ID NO 40
<211> LENGTH: 9
<212> TYPE: PRT
<213> ORGANISM: Artificial Sequence
<220> FEATURE:
<223> OTHER INFORMATION: clot-targeting peptide example 31

<400> SEQUENCE: 40

Cys Pro Gly Tyr Leu Arg Ser Leu Cys
1               5
```

```
<210> SEQ ID NO 41
<211> LENGTH: 9
<212> TYPE: PRT
<213> ORGANISM: Artificial Sequence
<220> FEATURE:
<223> OTHER INFORMATION: clot-targeting peptide example 32

<400> SEQUENCE: 41

Cys Arg Gly Glu Ser Trp Pro Tyr Cys
1               5

<210> SEQ ID NO 42
<211> LENGTH: 5
<212> TYPE: PRT
<213> ORGANISM: Artificial Sequence
<220> FEATURE:
<223> OTHER INFORMATION: clot-targeting peptide example 33

<400> SEQUENCE: 42

Cys Arg Glu Lys Ala
1               5

<210> SEQ ID NO 43
<211> LENGTH: 9
<212> TYPE: PRT
<213> ORGANISM: Artificial Sequence
<220> FEATURE:
<223> OTHER INFORMATION: clot-targeting peptide example 34

<400> SEQUENCE: 43

Cys Ala Arg Ser Lys Asn Lys Asp Cys
1               5

<210> SEQ ID NO 44
<211> LENGTH: 6
<212> TYPE: PRT
<213> ORGANISM: Artificial Sequence
<220> FEATURE:
<223> OTHER INFORMATION: clot-targeting peptide example 35

<400> SEQUENCE: 44

Cys Arg Lys Asp Lys Cys
1               5

<210> SEQ ID NO 45
<211> LENGTH: 10
<212> TYPE: PRT
<213> ORGANISM: Artificial Sequence
<220> FEATURE:
<223> OTHER INFORMATION: clot-targeting peptide example 36

<400> SEQUENCE: 45

Cys Gly Leu Ile Ile Gln Lys Asn Glu Cys
1               5                   10

<210> SEQ ID NO 46
<211> LENGTH: 10
<212> TYPE: PRT
<213> ORGANISM: Artificial Sequence
<220> FEATURE:
<223> OTHER INFORMATION: clot-targeting peptide example 37

<400> SEQUENCE: 46

Cys Asn Ala Gly Glu Ser Ser Lys Asn Cys
1               5                   10
```

FUSION PEPTIDE COMPRISING THROMBUS-TARGETING PEPTIDE, FERRITIN FRAGMENT AND THROMBOLYTIC PEPTIDE, AND USE THEREOF

SEQUENCE LISTING

The present application contains a Sequence Listing which has been submitted electronically in ASCII format and is hereby incorporated by reference in its entirety. The ASCII copy, created on Jun. 29, 2021, is named OP19-0101 Sequence Listing Corrected.txt and is 22,456 bytes in size.

TECHNICAL FIELD

The present invention relates to a fusion peptide comprising a clot-targeting peptide, a ferritin fragment, and a thrombolytic peptide, and use thereof. More specifically, the present invention relates to a fusion peptide in which a clot-targeting peptide, a ferritin fragment, and a thrombolytic peptide are sequentially linked, and to a composition comprising the fusion peptide as an active ingredient for preventing or treating a thrombotic disease.

BACKGROUND ART

The present application claims priority from Korean Patent Application No. 10-2017-0002588 filed on 6 Jan. 2017 and Korean Patent Application No. 10-2017-0183222 filed on 28 Dec. 2017, the disclosures of which are incorporated herein by reference in their entities.

Thrombi formed in arteries and veins play a very important role in the pathogenesis of myocardial infarction, stroke, and thrombosis, and these diseases cause the deaths of one in four people worldwide. Once formed, the thrombi obstruct or slow a normal flow of blood to heart, brain, or other vital organs, and often results in fatal injury.

The development of tissue plasminogen activator (tPA) is one of the most important accomplishments in thrombolytic therapies. The tPA converts plasminogen to plasmin, which degrades fibrin clots to restore the normal flow of blood. The largest limitation in tPA therapies is an unspecific activation of circulating plasminogen, and consequently, may disrupt normal physiological homeostasis or cause systemic hemorrhages. Actually, it is reported that 20% of the stroke patients receiving tPA therapy undergo life-threatening intracranial hemorrhages.

In a case of plasmin that cannot be administered via intravenous injection due to an inhibitor present in the circulation system, the local administration of plasmin through a catheter to the thrombus formation site results in direct dissolution of thrombus, and thereafter, any plasmin present in the circulation system is also rapidly neutralized to reduce side effects, such as hemorrhages. The use of such a catheter, however, has another limitation in that it requires an invasive surgical procedure.

Therefore, there is an urgent need to develop a novel concept of thrombolytic agents that show excellent thrombolytic activity, specifically act on thrombus formation sites, and consequently, cause no problems, such as life-threatening hemorrhages.

DETAILED DESCRIPTION OF THE INVENTION

Technical Problem

Accordingly, the present inventors endeavored to develop a fusion peptide showing excellent thrombolytic activity while specifically targeting a thrombus formation site, and as a result, found that a fusion peptide in which a clot-targeting peptide and a thrombolytic peptide, such as microplasminogen, are linked to both termini of a human ferritin fragment, shows excellent anti-thrombolytic activity, and thus completed the present invention.

Therefore, an aspect of the present invention is to provide a fusion peptide comprising: (a) a clot-targeting peptide; (b) any one peptide selected from the group consisting of ferritin fragments defined by the amino acid sequences of SEQ ID NO: 3 and SEQ ID NO: 4 and mutants thereof; and (c) any one peptide selected from the group consisting of microplasminogen, microplasmin, and mutants thereof, wherein the peptides (a), (b), and (c) are sequentially linked.

Another aspect of the present invention is to provide a cage protein consisting of the fusion peptides.

Another aspect of the present invention is to provide a polynucleotide encoding the fusion polypeptide.

Another aspect of the present invention is to provide an expression vector comprising the polynucleotide.

Another aspect of the present invention is to provide host cells transformed with the expression vector.

Another aspect of the present invention is to provide a pharmaceutical composition comprising the fusion peptide as an active ingredient for preventing or treating a thrombotic disease.

Another aspect of the present invention is to provide use of the fusion peptide for preparing an agent for treating a thrombotic disease.

Another aspect of the present invention is to provide a method for treating a thrombotic disease in a subject in need thereof, the method comprising administering the fusion protein to the subject in an amount effective for treating the thrombotic disease.

Technical Solution

In accordance with an aspect of the present invention, there is provided a fusion peptide comprising: (a) a clot-targeting peptide; (b) any one peptide selected from the group consisting of ferritin fragments defined by the amino acid sequences of SEQ ID NO: 3 and SEQ ID NO: 4 and mutants thereof; and (c) any one peptide selected from the group consisting of microplasminogen, microplasmin, and mutants thereof, wherein the peptides (a), (b), and (c) are sequentially linked.

In accordance with another aspect of the present invention, there is provided a cage protein consisting of the fusion peptides.

In accordance with another aspect of the present invention, there is provided a polynucleotide encoding the fusion polypeptide.

In accordance with another aspect of the present invention, there is provided an expression vector comprising the polynucleotide.

In accordance with another aspect of the present invention, there is provided host cells transformed with the expression vector.

In accordance with another aspect of the present invention, there is provided a pharmaceutical composition comprising the fusion peptide as an active ingredient for preventing or treating a thrombotic disease.

In accordance with another aspect of the present invention, there is provided use of the fusion peptide for preparing an agent for treating a thrombotic disease.

In accordance with another aspect of the present invention, there is provided a method for treating a thrombotic disease in a subject in need thereof, the method comprising administering the fusion peptide to the subject in an amount effective amount for treating the thrombotic disease.

Hereinafter, the present invention will be described in detail.

The present invention provides a fusion peptide, comprising: (a) a clot-targeting peptide; (b) any one peptide selected from the group consisting of ferritin fragments defined by the amino acid sequences of SEQ ID NO: 3 and SEQ ID NO: 4 and mutants thereof; and (c) any one peptide selected from the group consisting of microplasminogen, microplasmin, and mutants thereof, wherein the peptides (a), (b), and (c) are sequentially linked.

As used herein, the term "thrombus (or blood clot)" refers to a final product that is produced by hemostasis through blood coagulation. This substance is a dark red clot formed by coagulation resulting from aggregation and agglutination of platelets and fibrin due to the activation of the blood coagulation mechanism (i.e., coagulation factors). The collected blood, when left without separate treatments, coagulates to produce a coagulated product, which is often called a blood clot, and the coagulated product in the body is called a thrombus. The lump produced in the body usually spontaneously dissipate through fibrinolysis, but the pathogenically produced lump cannot be sufficiently dissolved in the body due an increased production amount thereof, and thus freely float in the whole body and block blood vessels, causing several thrombotic diseases.

A brief summary of the mechanism by which blood coagulates under normal conditions is as follows:

1. When a blood vessel is damaged, blood is exposed to air and platelets are destroyed.
2. An enzyme in the platelets is released to convert prothrombin (inactivated enzyme) to thrombin (activated enzyme) together with calcium ions.
3. The thrombin activated in the above stage converts fibrinogen (circular protein) into fibrin (linear protein).
4. The fibrin is tangled and polymerized with blood cells to produce a blood clot, and a blood clot formation site constricts, resulting in blood coagulation.

The blood coagulation occurring by the above-mentioned mechanism causes no particular problems in the normal bleeding state, but blood begins to coagulate from a specific site in the blood vessel in pathological conditions, such as damage or inflammation of the vascular endothelium, abnormalities resulting from arteriosclerosis, stagnation of blood, and increased blood coagulation caused by various factors (thrombogenesis). The thrombus formed in these pathological conditions narrows or blocks blood vessels to slow the normal flow of blood or completely occlude blood vessels. Representative examples of thrombotic diseases are: myocardial infarction that occurs when the flow of blood to the heart is not normal due to the thrombi formed in the coronary artery of the heart; and ischemic stroke (cerebral infarction) that occurs when thrombi are formed in the brain. Sometimes, thrombi fall off the blood vessel wall, and travel through the blood vessels to block downstream blood vessels, causing peripheral disorders.

In the present invention, for the clot-targeting peptide (CLT) (a), any peptide may be included in the present invention without limitation as long as it is a peptide showing a function capable of specifically targeting such thrombi, and a fibrin-binding peptide may also be included in the clot-targeting peptide. Non-limiting examples thereof are disclosed in the following literature:

Non-limiting examples thereof are disclosed in the following literature:

1) CN 101,190,940:

YIGSRRGDS, (SEQ ID NO: 10)

YIGSRRGDV, (SEQ ID NO: 11)

YIGSRRGDF, (SEQ ID NO: 12)

YIGSRYIGSK, (SEQ ID NO: 13)

YIGSRYIGSR, (SEQ ID NO: 14)

YIGSKRGDS, (SEQ ID NO: 15)

YIGSKRGDF, (SEQ ID NO: 16)

YIGSKRGDV, (SEQ ID NO: 17)

YIGSKYIGSK, (SEQ ID NO: 18)

YIGSKYIGSR, (SEQ ID NO: 19)

RGDSRGDS, (SEQ ID NO: 20)

RGDVRGDV, (SEQ ID NO: 21)

RGDFRGDF, (SEQ ID NO: 22)

RGDSYIGSR, (SEQ ID NO: 23)

RGDSYIGSK, (SEQ ID NO: 24)

RGDVYIGSR, (SEQ ID NO: 25)

RGDVYIGSK, (SEQ ID NO: 26)

RGDFYIGSR, (SEQ ID NO: 27)

RGDFYIGSK. (SEQ ID NO: 28)

2) US 6,984,373 B2:

CSDENWLWC, (SEQ ID NO: 29)

CPMSEWLYC, (SEQ ID NO: 30)

CPWESWTFC, (SEQ ID NO: 31)

CQEEPWLFC, (SEQ ID NO: 32)

CPGEDWLFC, (SEQ ID NO: 33)

CTGEPGPIC, (SEQ ID NO: 34)

CQLGYRTYC, (SEQ ID NO: 35)

-continued

CDGEPWLFC, (SEQ ID NO: 36)

CGWGSWKFC, (SEQ ID NO: 37)

CGWGSGKLC, (SEQ ID NO: 38)

CPGEPWTFC, (SEQ ID NO: 39)

CPGYLRSLC, (SEQ ID NO: 40)

CRGESWPYC. (SEQ ID NO: 41)

3) US 8,912,136 B2:

CREKA, (SEQ ID NO: 42)

CARSKNKDC, (SEQ ID NO: 43)

CRKDKC (SEQ ID NO: 44)

4) EP 1,986,682 B1:

CGLIIQKNEC, (SEQ ID NO: 45)

CNAGESSKNC (SEQ ID NO: 46)

Preferably, the clot-targeting peptide in the present invention may be a peptide defined by the amino acid sequence of SEQ ID NO: 1 (CNAGESSKNC) or SEQ ID NO: 2 (CGLIIQKNEC) or a mutant thereof, and most preferably, may be the peptide of SEQ ID NO: 1 or a mutant thereof, but is not limited thereto.

As used herein, the term "mutant" refers to a peptide showing substantially the same physiological activity as the peptide. The term "same physiological activity" refers to having at least 60%, preferably at least 70%, and more preferably at least 90% sequence homology while having isomerization ability. In addition, the term "mutant" includes amino acid sequence variants obtained by substitution of some or all of amino acids of a natural type protein or by deletion or addition of some of amino acids. The substitution of amino acids is preferably a conservative substitution. Examples of the conservative substitution of naturally existing amino acids are as follows: aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn), and sulfur-containing amino acids (Cys, Met). In addition, a structural modification for changing stability, storageability, volatility, or solubility of the peptide of the present invention and a fusion protein produced by fusion with another protein, such as GFP, with maintenance of physiological activity are included in the above-described examples.

Therefore, the "mutant" in the present invention refers to a peptide that retains physiological activity to target clots while having at least 60%, preferably at least 70%, and more preferably at least 90% amino acid sequence homology with the peptide of SEQ ID NO: 1 or SEQ ID NO: 2.

The term "ferritin protein" in the present invention is a kind of intracellular proteins and functions to store and release iron. Ferritin is generally in the form of a hollow spherical cage in vivo, and the cage consists of 24 ferritin monomers. The ferritin monomers are classified into heavy chain monomers and light chain monomers depending on the structure thereof.

In the present invention, for the ferritin protein, any protein may be used without limitation as long as it has activity to form a cage form of complex protein as a unit, and the average molecular weight thereof may be, but not limited to, 20-25 kDa. More preferably, the ferritin protein may be at least one selected from the group consisting of GenBank accession No: AAA62259.1 (ferritin light chain, mouse,), NCBI accession No: NP_071945.3 (ferritin light chain, rat), NCBI accession No: NP_001108012.1 (ferritin light chain, horse), NCBI accession No: NP_002023.2 (ferritin heavy chain, human), NCBI accession No: NP_034369.1 (ferritin heavy chain, mouse), NCBI accession No: NP_036980.1 (ferritin heavy chain, rat), and NCBI accession No: NP_001093883.1 (ferritin heavy chain, horse). The ferritin protein may be more preferably a human-derived ferritin monomer light chain (SEQ ID NO: 8) or a human-derived ferritin monomer heavy chain (SEQ ID NO: 9), and most preferably, the human-derived ferritin monomer light chain (SEQ ID NO: 8), but is not limited thereto.

SEQ ID NO: 8 (Human-derived ferritin monomer light chain):
mssqirqnys tdveaavnsl vnlylqasyt ylslgfyfdr ddvalegvsh ffrelaeekr egyerllkmq nqrggralfq dikkpaedew gktpdamkaa malekklnqa lldlhalgsa rtdphlcdfl ethfldeevk likkmgdhlt nlhrlggpea glgeylferl tlkhd SEQ ID NO: 9 (Human-derived ferritin monomer heavy chain):
MTTASTSQVR QNYHQDSEAA INRQINLELY ASYVYLSMSY

YFDRDDVALK NFAKYFLHQS HEEREHAEKL MKLQNQRGGR

IFLQDIKKPD CDDWESGLNA MECALHLEKN VNQSLLELHK

LATDKNDPHL CDFIETHYLN EQVKAIKELG DHVTNLRKMG

APESGLAEYL FDKHTLGDSD NES

In the present invention, the "ferritin fragment" in (b) is not limited as long as it retains activity to form a cage form of complex protein, but may comprise A-helix, B-helix, C-helix, and D-helix in the wild-type ferritin protein. In other words, the ferritin fragment refers to a short ferritin in the form in which E-helix is removed out of A-, B-, C-, D-, and E-helixes constituting the wild-type ferritin. Preferably, the ferritin fragment may be a ferritin fragment in which one or more of amino acid residues after position 160 in the amino acid sequence of the human-derived ferritin monomer light chain (SEQ ID NO: 8) are removed or one or more of amino acid residues after position 165 in the amino acid sequence of the human-derived ferritin monomer heavy chain (SEQ ID NO: 9) are removed. More preferably, the ferritin fragment may be a ferritin fragment in which one or more of amino acid residues after position 158 in the amino acid sequence of SEQ ID NO: 8 are removed or one or more of amino acid residues after position 162 in the amino acid sequence of SEQ ID NO: 9 are removed. Most preferably, the ferritin fragment may be defined by the amino acid sequence of SEQ ID NO: 3 or 4.

SEQ ID NO: 3 (Human-derived ferritin light chain fragment):
mssqirqnys tdveaavnsl vnlylqasyt ylslgfyfdr ddvalegvsh ffrelaeekr egyerllkmq nqrggralfq dikkpaedew gktpdamkaa malekklnqa lldlhalgsa rtdphlcdfl ethfldeevk likkmgdhlt nlhrlgg SEQ ID NO: 4 (Human-derived ferritin heavy chain fragment):
MTTASTSQVR QNYHQDSEAA INRQINLELY ASYVYLSMSY

YFDRDDVALK NFAKYFLHQS HEEREHAEKL MKLQNQRGGR

IFLQDIKKPD CDDWESGLNA MECALHLEKN VNQSLLELHK

LATDKNDPHL CDFIETHYLN EQVKAIKELG DHVTNLRKMG A

As used herein, the "mutant" in (b) refers to a peptide that retains activity to form a cage form of complex protein while having at least 60%, preferably at least 70%, and more preferably at least 90% amino acid sequence homology with the peptide of SEQ ID NO: 3 or SEQ ID NO: 4.

Plasminogen is an inactive precursor of plasmin, which is a fundamental fibrinolytic enzyme in mammals. Plasmin performs an important role in cell migration, tissue remodeling, and bacterial invasion. Plasmin is a serine protease that preferentially cleaves between Lys-Xaa and Arg-Xaa with higher selectivity than trypsin. Plasminogen activators, for example, plasminogen activator (tPA) or urokinase, cleave the Arg 560-Val 561 bond of the human plasminogen molecule to produce active plasmin. Two chains of the produced plasmin are linked together by an interchain disulphide linkage. The light chain (25 kDa) carries the catalytic center (comprising the catalytic triad) and shares sequence similarity with trypsin and other serine proteases. The heavy chain (60 kDa) consists of five highly similar triple-loop structures called kringles. Some of the kringles comprise lysine binding sites mediating the plasminogen/plasmin interaction with fibrin. Plasmin belongs to peptidase family S1.

Plasminogen, an inactivated enzyme, is a protein consisting of a total of 810 amino acids (GenBank: AAA60113.1). Plasminogen consists of pre-activation peptide (PAP) at the N-terminus, five kringle domains, and a serine protease domain at the C-terminus. When fibrin or other receptor is in a first contact with kringle domain-1, the five kringle domains are rearranged into an open confirmation thereof, and such rearrangement allows plasminogen activators, such as tPA and urokinase, to have access to plasminogen.

Microplasminogen (or microplasmin) is a short form of plasminogen (or plasmin) that retains the protease domain of plasminogen (or plasmin) but lacks the five kringle domains constituting the primary binding site of fibrin and antiplasmin. In the present invention, the microplasminogen (or microplasmin) exhibits thrombolytic activity and thus shows an effect of removing thrombi at the thrombus formation site.

In the present invention, the microplasminogen or microplasmin may include, without limitation, any form in which five kringle domains are removed from wild-type plasminogen or plasmin, and mutants thereof may also be used for the fusion protein of the present invention. In the present invention, the "mutant" refers to a peptide that retains physiological activity to dissolve thrombi while having at least 60%, preferably at least 70%, and more preferably at least 90% amino acid sequence homology with microplasminogen or microplasmin.

Specific examples of the mutant of the microplasminogen can be easily conceived by a person skilled in the art through prior art documents. For example, Wang et al. (1995, Protein Science 4, 1758-1767 and 1768-1779) have reported an extensive series of microplasminogen mutants in which mutation occurs at amino acid positions 545, 548, 550, 555, 556, 558, 560-564, 585, 740, and 788. A double mutant in which serine is substituted with cysteine at amino acid positions 558 and 566 has been reported by Linde et al. (1998, Eur J Biochem 251, 472-479). Jespers et al. (1998, Biochemistry 37, 6380-6386) has produced, in an Ala-scan, the series of phage-displayed microplasminogen single-site mutants H569A, R610A, K615A, D660A, Y672A, R712A, R719A, T782A, and R789A.

In the present invention, the microplasminogen may be, preferably, consist of amino acids at positions 561-810 out of 810 amino acids constituting the wild-type human plasminogen (Sequence ID: AAA60113.1), and may be, more preferably, defined by the amino acid sequence of SEQ ID NO: 5. In the present invention, the microplasmin may be preferably defined by the amino acid sequence of SEQ ID NO: 6.

SEQ ID NO: 5 (microplasminogen):
AAPSFDCGKP QVEPKKCPGR VVGGCVAHPH SWPWQVSLRT

RFGMHFCGGT LISPEWVLTA AHCLEKSPRP SSYKVILGAH

QEVNLEPHVQ EIEVSRLFLE PTRKDIALLK LSSPAVITDK

VIPACLPSPN YVVADRTECF ITGWGETQGT FGAGLLKEAQ

LPVIENKVCN RYEFLNGRVQ STELCAGHLA GGTDSCQGDS

GGPLVCFEKD KYILQGVTSW GLGCARPNKP GVYVRVSRPV

TWIEGVMRNN

SEQ ID NO: 6 (microplasmin):
VVGGCVAHPH SWPWQVSLRT RFGMHFCGGT LISPEWVLTA

AHCLEKSPRP SSYKVILGAH QEVNLEPHVQ EIEVSRLFLE

PTRKDIALLK LSSPAVITDK VIPACLPSPN YVVADRTECF

ITGWGETQGT FGAGLLKEAQ LPVIENKVCN RYEFLNGRVQ

STELCAGHLA GGTDSCQGDS GGPLVCFEKD KYILQGVTSW

GLGCARPNKP GVYVRVSRFV TWIEGVMRNN

In the present invention, the sequential linkage of the peptides (a), (b), and (c) means that when the peptide (a) is linked to the N-terminus of the ferritin fragment, the peptide (c) is linked to the C-terminus thereof, and vice versa. Preferably, in the fusion protein, the clot-targeting peptide (a) is linked to the N-terminus of the ferritin fragment or the mutant thereof in (b), and the peptide (c), which is selected from the group consisting of microplasminogen, microplasmin, and mutants thereof, is linked to the C-terminus of the ferritin fragment or the mutant thereof in (b).

A gene for obtaining the peptide of the present invention may be isolated from genomic DNA or cDNA of any source and preferably human or mouse cDNA or genomic library. A general method for obtaining a gene encoding the peptide of the present invention is well described in the art (see: Sambrook, Fitsch & Manatis, Molecular Cloning: A Laboratory Manual, Second Edition (1989)). In addition, any animal cell can be provided as a nucleic acid source for molecular cloning of the gene encoding the peptide of the present invention. The DNA may be obtained from cloned DNA by known techniques, and preferably, DNA may be obtained from a cDNA library prepared from cells with high level expression of the protein by chemical synthesis, by cDNA cloning, or by the cloning of genomic DNA, or fragments thereof, purified from the desired cells [Sambrook et al., 1989, supra: Glover, D. M. (ed). 1985, DNA Cloning; A Practical Approach. MRL Press. Ltd., Oxford. U. K. Vol. I, II]. Cloned genes from genomic DNA may comprise regulatory and intron DNA regions in addition to coding regions. Cloned genes from cDNA do not comprise intron sequences. Whatever the source, the gene should be molecularly cloned into a suitable vector for delivery of the gene.

The peptides of the present invention may be prepared by a person skilled in the art through known methods. These peptides are usually parts of a larger polypeptide and may be produced in prokaryotic or eukaryotic cells by expressing polynucleotides encoding the peptide sequences of the present invention.

As another method, these peptides may be produced by chemical synthesis. The expression of xenoproteins in recombinant hosts, chemical synthesis of polypeptides, and a method for in vitro transcription are well known in the art, and are further described in the followed literature (References: Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11: 255; Kaiser et al. (1989) Ann. Rev. Biochem. 57:957; and Offord, R. E. (1980) Semisynthetic Proteins, Wiley Publishing).

In the present invention, the clot-targeting peptide (a) or the peptide (c), which is selected from the group consisting of microplasminogen, microplasmin, and mutants thereof, is linked to the ferritin fragment or the mutant thereof in (b) via a linker.

The linker refers to a naturally derived peptide linker or a synthetically derived peptide linker. The peptide linker consists of linear amino acid chains, wherein 20 types of naturally occurring amino acids are monomeric building blocks. The linker may have a repetitive amino acid sequence or may have a naturally occurring polypeptide, for example, a polypeptide sequence having a hinge function. All peptide linkers may be encoded by nucleic acid molecules, and thus may be expressed in a recombinant manner. Since the linker per se is a peptide, the respective peptides are linked to the linker through peptide linkages.

The linker consists of amino acids linked together via peptide linkages, and preferably, 1 to 20 amino acids linked together via peptide linkages, wherein the amino acids are selected from 20 natural amino acids. Of these amino acids, at least one is glycosylated as understood by a person skilled in the art. Preferably, the 1-20 amino acids are selected from glycine, alanine, proline, asparagine, glutamine, and lysine, but are not limited thereto.

In an example of the present invention, a fusion protein having the amino acid sequence of SEQ ID NO: 7 was fabricated, and activity thereof was evaluated.

SEQ ID NO: 7 (fusion peptide):
MGGT<u>CNAGESSKNC</u>ASGHM*SSQIRQNYSTDVEAAVNSLVNLYLQASYTYL*

*SLGFYFDRDDVALEGVSHFFRELAEEKREGYERLLKMQNQRGGRIFLQDI*

*KKPAEDEWGKTPDAMKAAMALEKKLNQALLDLHALGSARDTPHLCDFLET*

*HFLDEEVKLIKKMGDHLTNLHRLGGG*SEFVDGGGSGTSAAPSFDCGKPQV

EPKKCPGRVVGGCVAHPHSWPWQVSLRTRFMGHFCGGTLISPEWVLTAAH

CLEKSPRPSSYKVILGAHQEVNLEPHVQEIEVSRLFLEPTRKDIALLKLS

SPAVITDKVIPACLPSPNYVVADRTECFITGWGETQGTFGAGLLKEAQLP

VIENKVCNRYEFLNGRVQSTELCAGHLAGGTDSCQGDSGGPLVCFEKDKY

ILQGVTSWGLGCARPNKPGVYVRVSRFVTWIEGVMRNNLEHHHHHH (Underlined: CLT2 peptides/Italic type:

s-ferritin/Bold type: microplasminogen)

The present invention provides a cage protein consisting of the fusion peptides.

The protein cage is formed by a precise self-assembly property of low-molecular weight monomers, and is a cage consisting of a protein and having a space inside. A viral capsid protein, ferritin, a heat shock protein, or Dps protein corresponds to this protein cage. The protein cage of the present invention comprises the fusion polypeptides of the present invention as a monomer constituting the protein cage. As used herein, the term "self-assembly" refers to a property of certain molecules to form a specific nanostructure spontaneously without external particular stimuli or artificial induction.

The protein cage of the present invention is formed by the binding of the fusion proteins of the present invention, and is generally in the form of a spherical cage in vivo.

The protein cage of the present invention may be a complex protein in which the fusion peptides of the present invention are regularly arranged as monomers, and may be formed by a three-dimensional regular arrangement of 24 fusion proteins of the present invention. When the fusion proteins of the present invention form a protein cage by self-assembly, the clot-targeting peptide and microplasminogen or the like, which are linked to the C-terminus and the N-terminus of the ferritin fragment, respectively, retain physiological activity thereof intact.

According to an example of the present invention, a fusion peptide (CLT-sFt-μPg), in which a clot-targeting peptide (CLT), a human-derived ferritin light chain fragment (sFt), and microplasminogen (μPg) are sequentially linked, was constructed, and it was confirmed that a cage protein was formed through a three-dimensional arrangement of the 24 fusion peptides each as a monomer. It was confirmed that the CLT peptide linked to the N-terminus of sFt was exposed to the outside of the cage protein and the microplasminogen fused to the C-terminus thereof was clustered in a 4-fold symmetry and exposed in a petal-like appearance to the outside of the cage protein. Meanwhile, it was confirmed that the microplasminogen exposed to the outside of the cage protein is oriented in such a direction as to retain an active cleavage site (Arg-Val).

That is, it can be seen that the fusion peptides of the present invention do not interfere with the characteristics of wild-type ferritin monomers to form a ferritin cage protein by the self-assembly property, and still form a cage protein well.

The present invention provides a polynucleotide encoding the fusion peptide.

As for the polynucleotide, any polypeptide may be used without limitation as long as it encodes the fusion protein of the present invention, and includes all of DNA, cDNA, and RNA sequences. The polynucleotide may be isolated from nature and may be prepared by a genetic engineering method known in the art.

The present invention also provides an expression vector comprising the polynucleotide.

As used herein, the term "vector" refers to a DNA construct that contains a DNA sequence operably linked to a suitable regulatory sequence capable of expressing DNA in a suitable host. The vector may be a plasmid, a phage particle, or simply a potential genomic insert. Once transformed into a suitable host, the vector can replicate and function regardless of the host genome, or may, in some cases, integrate into the genome itself. In the present specification, "plasmid" and "vector" are sometimes used interchangeably since the plasmid is currently the most commonly used form of vector. For the purpose of the present invention, the plasmid vector is preferably used. A typical plasmid vector that can be used for this purpose retains a structure comprising: (a) replication origins at which efficient replication occurs so as to contain several hundreds of plasmid vectors per host cell; (b) an antibiotic-resistant gene by which host cells transformed with the plasmid vector can be selected; and (c) restriction enzyme cleavage sites into which foreign DNA fragments can be inserted. Even if suitable restriction enzyme cleavage sites are not present in the vector, the use of a synthetic oligonucleotide adaptor or linker according to a typical method enables easy ligation of the vector and a foreign DNA fragment.

The vector of the present invention includes a plasmid vector, a cosmid vector, a bacteriophage vector, and a viral vector, but is not limited thereto. A suitable vector is an expression vector, and may comprise expression regulatory elements, such as a promoter, an operator, an initiation codon, a stop codon, a polyadenylation signal, and an enhancer, and a variety of vectors can be constructed according to the purpose. The vector of the present invention corresponds to any measure that is used to deliver a nucleic acid encoding the peptide of the present invention into host cells, and preferable examples of the vector are viral vectors, such as retroviral, herpes viral, adenoviral, and adeno-associated viral vectors. Therefore, the gene encoding the peptide of the present invention is introduced in vivo, ex vivo and in vitro by using viral vectors or the direct introduction of DNA. The expression in the target tissue may be performed by targeting a mutant vector to specific cells through using a viral vector or receptor ligand, by using tissue-specific promoter, or by using both.

The standard recombinant DNA and molecular cloning techniques used in the present invention are widely known in the art, and disclosed in the following literature (Sambrook, J., Fritsch, E. F. and Maniatis, T., Molecular Cloning: A Laboratory Manual, 2nd ed., Cold Spring Harbor Laboratory: Cold Spring Harbor, N.Y. (1989); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987)).

Furthermore, the present invention provides host cells transformed with the expression vector.

For the host cells, host cells that control the expression of an inserted sequence or produce in a preferable specific manner a genetic product may be selected. Different host cells have characteristic and specific mechanisms for protein translation, post-translational processing, and transformation. For a suitable cell line or host system, a cell line or host system that provides preferable transformation and processing of expressed heterologous proteins may be selected. The expression in yeasts can produce biologically active products. The expression in eukaryotic cells can increase the likelihood of "natural" folding.

Any host cell known in the art may be used as a host cell as long as it can perform continuous cloning and expression while stabilizing the vector of the present invention. For example, E. coli JM109, E. coli BL21DE, E. coli DH5, E. coli RR1, E. coli LE392, E. coli B, E. coli X 1776, and E. coli W3110 may be used. Also, Agrobacterium spp. strains (such as Agrobacterium A4), Bacilli spp. strains (such as Bacillus subtilis), other intestinal bacteria, such as Salmonella typhimurium or Serratia marcescens, and various Pseudomonas spp. strains may be used as host cells.

Any known method by which a vector is transferred into host cells to transform the host cells may be employed, without particular limitation. For example, the host cells may be transformed with calcium phosphate precipitation, a DEAE-dextran method, electroporation, direct microinjection, a DNA-loaded liposome method, a lipofectamine-DNA complex method, cell sonication, gene bombardment using high-velocity microprojectiles, a polycation method, and receptor-mediated transfection. Some of these techniques may be modified for use in vivo or in vitro.

The vector injected into the host cells may be expressed in the host cells, and in this case, a large quantity of recombinant peptides or proteins is obtained. For example, in cases where the vector comprises the lac promoter, gene expression can be induced by treatment of host cells with IPTG.

In the method of the present invention, the transgenic host cells can be incubated using a medium that is usually used in the art. For example, in cases where the host cells were prokaryotic cells (e.g., E. coli), the host cells may be incubated using Luria-Bertani (LB) medium. In cases where the host cells are animal cells, transformants may be incubated using Eagle's minimum essential medium (Eagle's MEM, Eagle, H. Science 130:432(1959)). Various incubation methods for host cells are well known in the art, and disclosed in Sambrook et al., Molecular Cloning, A Laboratory Manual, Cold Spring Harbor Laboratory Press (2001), which is incorporated herein by reference.

The fusion peptide of the present invention is very effective in targeting and dissolving thrombi. According to an example of the present invention, it could be confirmed that the fusion protein of the present invention had (i) excellent clot-targeting activity, (ii) excellent thrombolytic activity, and (iii) low susceptibility to inactivation of microplasmin by anti-plasmin.

Specifically, according to an example of the present invention, as for clot-targeting activity, the clot-binding ability of the cage protein formed by CLT-sFt-µPg monomers was significantly higher than that of the CLT-µPg fusion protein, meaning that the CLT peptide of the cage surface targets clots with higher affinity through the augmentation of binding activity by the cage structure.

According to another example of the present invention, it was investigated, by monitoring the level of circulating α2-anti-plasmin, whether the nanocage protein structure can shield the activated μPn from being degraded by anti-plasmin in the blood. As a result, the level of circulating α2-anti-plasmin decreased more slowly following intravenous administration of the activated CLT-sFt-μPn DCNC, when compared with the administration of free form of μPn. These results mean that the nanocage structure shielded the activated μPn from being degraded by anti-plasmin.

In another example of the present invention, the thrombolytic activity of the fusion peptide was evaluated in in-vivo arterial thrombotic animal models and venous thrombotic animal models. As a result, it could be confirmed that the cage protein formed by the CLT-sFt-μPg monomers of the present invention dissolve arterial and venous thrombi very effectively. Meanwhile, CLT-μPg in a form of not being linked to sFt did not show a clot-targeting effect in vivo, unlike the in vitro targeting evaluation, and consequently, showed very low thrombolytic activity. That is, it could be seen that the fusion of CLT targeting clots to μPg showing thrombolytic activity did not show clot-targeting lytic ability but the formation of the cage protein by sFt maintains excellent thrombolytic activity of μPn as well as clot targeting of the CLT peptide.

Therefore, the present invention provides a pharmaceutical composition comprising the fusion peptide as an active ingredient for preventing or treating a thrombotic disease.

As used herein, the "thrombotic disease" refers to any disease that is caused by thrombi, especially any disease that is caused by the blockage of arterial or venous blood vessels due to thrombi. Such a disease is known to be caused by factors, such as a slow blood flow, excessive coagulation, and vascular damage, alone or in combination, but is not limited thereto. Examples of the thrombotic disease are thrombosis, hypertension, stroke, cerebral infarction, angina pectoris, myocardial infarction, atherosclerosis, peripheral arterial atresia, renal vein occlusion, central retinal vein occlusion, pulmonary thrombosis, deep vein thrombosis, portal vein thrombosis, cerebral sinus thrombosis, cerebral atherosclerosis, heart disease, ischemic heart disease, intracranial hemorrhage, aneurysm, atherothrombosis, nephrosclerosis, and the like, and preferably include thrombosis caused by thrombi and platelet coagulation, hypertension, stroke, cerebral infarction, angina pectoris, myocardial infarction, atherosclerosis, or ischemic heart disease, but are not limited thereto.

The pharmaceutical composition according to the present invention may be formulated into a suitable form containing the fusion protein alone or together with a pharmaceutically acceptable carrier, and may further contain an excipient or a diluent. The term "pharmaceutically acceptable" composition refers to a composition that is physiologically acceptable, and when administered to humans, does not cause allergic responses, such as gastrointestinal disorder and vertigo, or similar reactions.

Examples of the pharmaceutically acceptable carrier may further include a carrier for oral administration or a carrier for parenteral administration. The carrier for oral administration may include lactose, starch, a cellulose derivative, magnesium stearate, stearic acid, and the like. In addition, the carrier for oral administration may include various drug delivery substances used for oral administration of peptide preparations. Also, the carrier for parenteral administration may include water, suitable oil, saline, aqueous glucose, and glycol, and may further include a stabilizer and a preservative. Suitable examples of the stabilizer include an antioxidant, such as sodium hydrogen sulfite, sodium sulfite, or ascorbic acid. Suitable examples of the preservative include benzalkonium chloride, methyl- or propyl-paraben, and chlorobutanol. The pharmaceutical composition of the present invention may further contain, in addition to the above ingredients, a lubricant, a wetting agent, a sweetening agent, a flavoring agent, an emulsifier, a suspending agent, and the like. Other pharmaceutically acceptable carriers and preparations may be referred to in the literature (Remington's Pharmaceutical Sciences, 19th ed., Mack Publishing Company, Easton, Pa., 1995).

The composition of the present invention may be administered to mammals including humans by any method. For example, the composition of the present invention may be administered orally or parenterally. The parental administration may be, but is not limited to, intravenous, intramuscular, intra-arterial, intramedullary, intradural, intracardiac, transdermal, subcutaneous, intraperitoneal, intranasal, intestinal, topical, sublingual, or rectal administration.

The pharmaceutical composition of the present invention may be formulated as a preparation for oral administration or parental administration according to the route of administration as described above.

For preparations for oral administration, the composition of the present invention may be formulated in forms of a powder, granules, a tablet, a pill, a sugar tablet, a capsule, a liquid, a gel, syrup, slurry, and a suspension, by the methods known in the art. For example, as for a preparation for oral administration, a tablet or sugar coated tablet may be obtained by mixing an active ingredient with a solid excipient, pulverizing the mixture, adding a suitable adjuvant thereto, and then processing the mixture into a granule mixture. Suitable examples of the excipient may include: sugars (including lactose, dextrose, sucrose, sorbitol, mannitol, xylitol, erythritol, and maltitol); starches (including corn starch, wheat starch, rice starch, and potato starch); celluloses (including cellulose, methyl cellulose, sodium carboxy methyl cellulose, and hydroxypropyl methyl cellulose); and fillers (such as gelatin and polyvinyl pyrrolidone). In some cases, cross-linked polyvinyl pyrrolidone, agar, alginic acid, sodium alginate, or the like may be added as a disintegrant. Furthermore, the pharmaceutical composition of the present invention may further contain an anti-coagulant, a slipping agent, a wetting agent, a favoring agent, an emulsifier, and a preservative.

For preparations for parental administration, the composition of the present invention may be formulated into forms of an injection, a cream, a lotion, an external ointment, oil, a moisturizer, a gel, an aerosol, and a nasal inhaler, by the methods known in the art. These formulations are described in the literature, which is a formulary generally known in all the pharmaceutical chemistry fields (Remington's Pharmaceutical Science, 19th ed., Mack Publishing Company, Easton, Pa., 1995).

A total effective amount of the composition of the present invention may be administered to a patient in a single dose, or in a multiple dose by a fractionated treatment protocol for a long period of time. In the pharmaceutical composition of the present invention, the content of the active ingredient may vary depending on the severity of disease. A total dosage of the pharmaceutical composition of the present invention may be preferably about 0.01 pg to 10,000 mg, and more preferably 0.1 pg to 500 mg relative to 1 kg of patient body weight per day. However, as for the dosage of the pharmaceutical composition, an effective dose thereof to a patient is determined considering various factors, such as the method for formulation, route of administration, number of times of treatment, as well as the age, weight, health condition, sex, severity of disease, diet, and excretion rate of the patient, and thus considering these factors, a person skilled in the art could determine a suitable effective dose of the composition of the present invention. The pharmaceutical composition according to the present invention is not particularly limited to the dosage form, route of administration, and administration method thereof.

The fusion peptide of the present invention may be administered together with a suitable anti-coagulant or a thrombotic agent, such as a plasminogen activator or streptokinase, to achieve a synergistic effect in the treatment of various thrombotic diseases.

The present invention provides use of the fusion protein for preparing an agent for treating a thrombotic disease.

The present invention provides a method for treating a thrombotic disease in a subject in need thereof, the method comprising administering the fusion peptide of any one of claims 1 to 6 to the subject in an amount effective for treating the thrombotic disease in the subject.

As used herein, the term "effective amount" refers to an amount showing an effect of alleviating, treating, preventing, detecting, or diagnosing a thrombotic disease when administered to a subject, and the term "subject" refers to an animal, preferably a mammal, especially an animal including a human being, and may be cells, a tissue, an organ, or the like derived from an animal. The subject may be a patient in need of the effect.

As used herein, the term "treating" refers collectively to alleviating a thrombotic disease, a thrombotic disease-related disease, or a symptom of the thrombotic disease-related disease, and may include healing, substantially preventing, or alleviating conditions of these diseases, and may include alleviating, curing, or preventing one or most of the symptoms resulting from a thrombotic disease or a thrombotic disease-related disease, but is not limited thereto.

As used herein, the term "comprising" is used synonymously with "containing" or "being characterized", and does not exclude additional ingredients or steps not mentioned in the compositions or methods. The term "consisting of" means excluding additional elements, steps, or ingredients not otherwise specified. The term "essentially consisting of" means comprising the mentioned elements or steps as well as any element or step that does not substantially affect basic characteristics thereof in compositions or methods.

Advantageous Effects

The fusion peptide of the present invention is very effective in targeting and dissolving thrombi and has no bleeding side effects, and thus can be favorably used in the development of an agent for preventing or treating a thrombotic disease with fewer side effects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Abbreviations used in all drawings are as follows:

CLT: clot-targeting peptide, sFt: ferritin fragment, μPg: microplasminogen, μPn: microplasmin, CLT-sFt-μ: fusion protein in which respective peptides are linked.

Figure 1A:
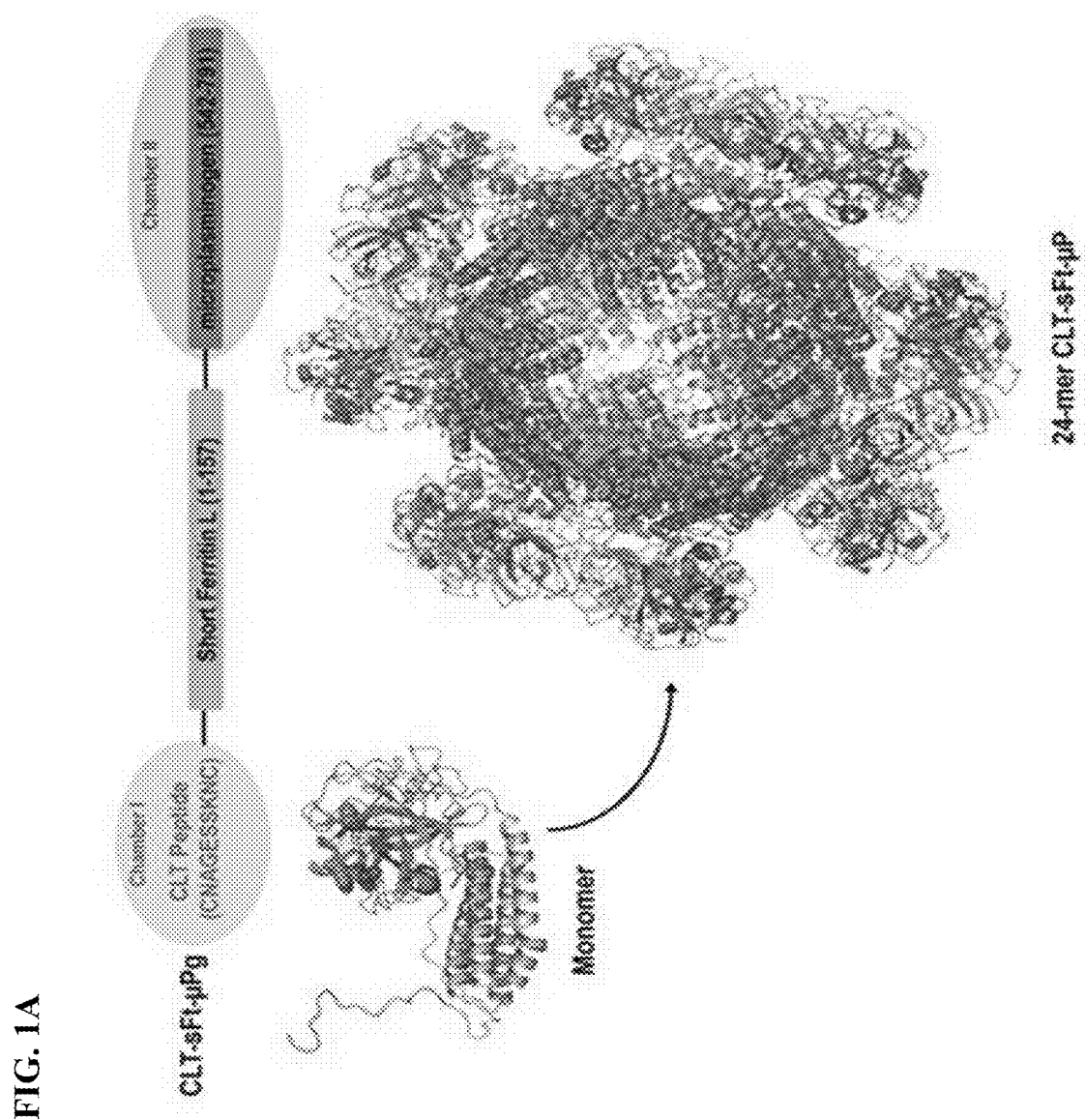

FIG. 1A is a diagram showing a schematic view of a fusion peptide monomer (CLT-sFt-μPg) according to the present invention and a cage formed by the monomers. The 3D structure of CLT-sFt-μPg was modeled using MODELLER v9.12 on the basis of the structures of human ferritin (PDB 2FG4) and microplasminogen (PDB 1QRZ). The CTL peptide (CNAGESSKNC (SEQ ID NO: 1)) is shown in red ribbon, the microplasminogen in green, and the ferritin fragment in light brown. The cleavage site ($Arg^{561}$-$Val^{562}$) by the plasminogen activator is shown in magenta, and the catalytic triad amino acid residues ($His^{603}$, $Asp^{646}$, and $Ser^{741}$) are shown in orange color.

Figure 1B:
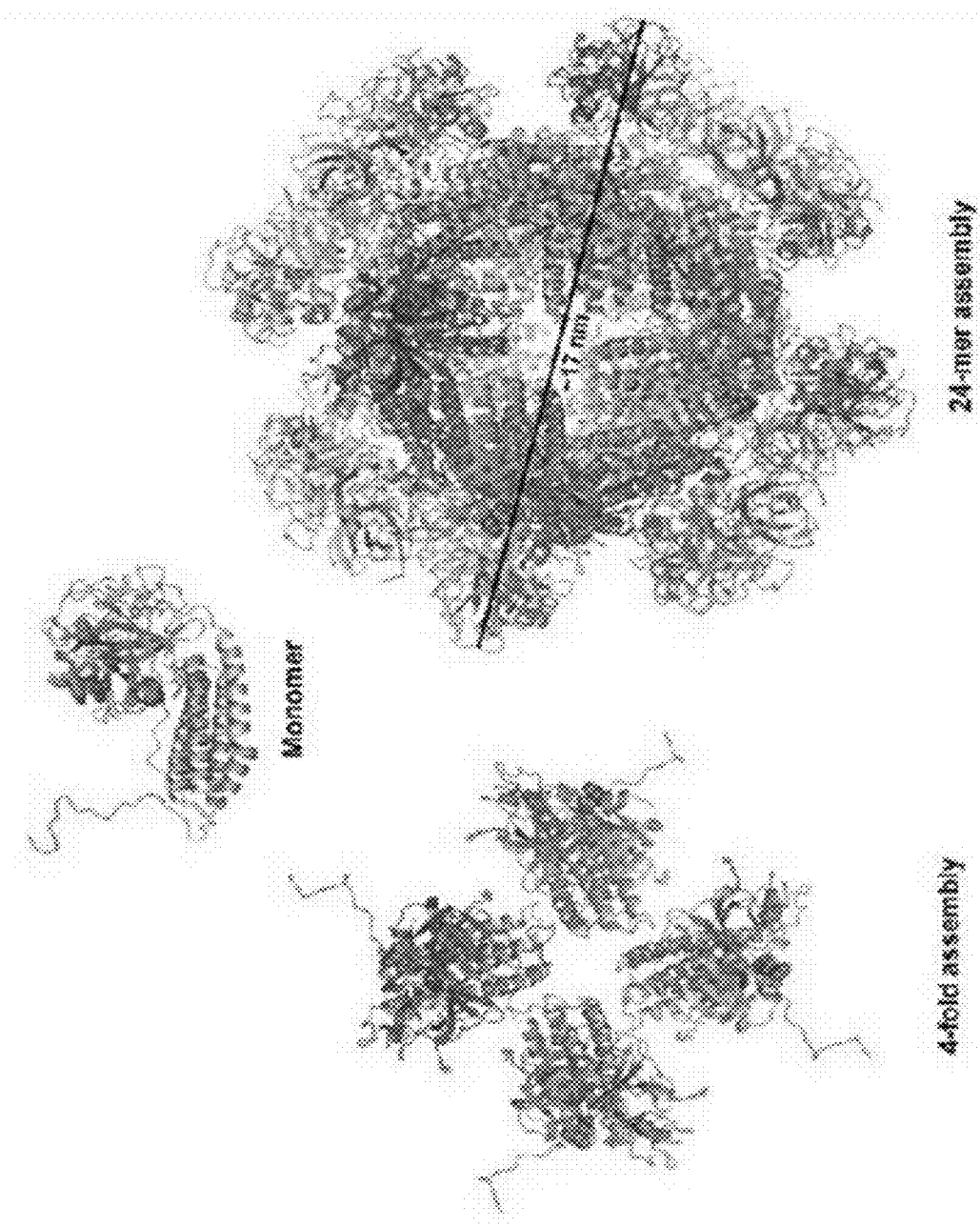

FIG. 1B is a design of an assembly of CLT-sFt-μPg monomers. It can be confirmed that six 4-fold assemblies of CLT-sFt-μPg monomers are assembled to form a cage, and microplasminogen fused to the C-terminus of the ferritin fragment and CLT protein fused to the N-terminus thereof are exposed to the outside. The diameter of the cage protein consisting of CLT-sFt-μPg fusion peptides was calculated to be about 17 nm.

Figure 2A:
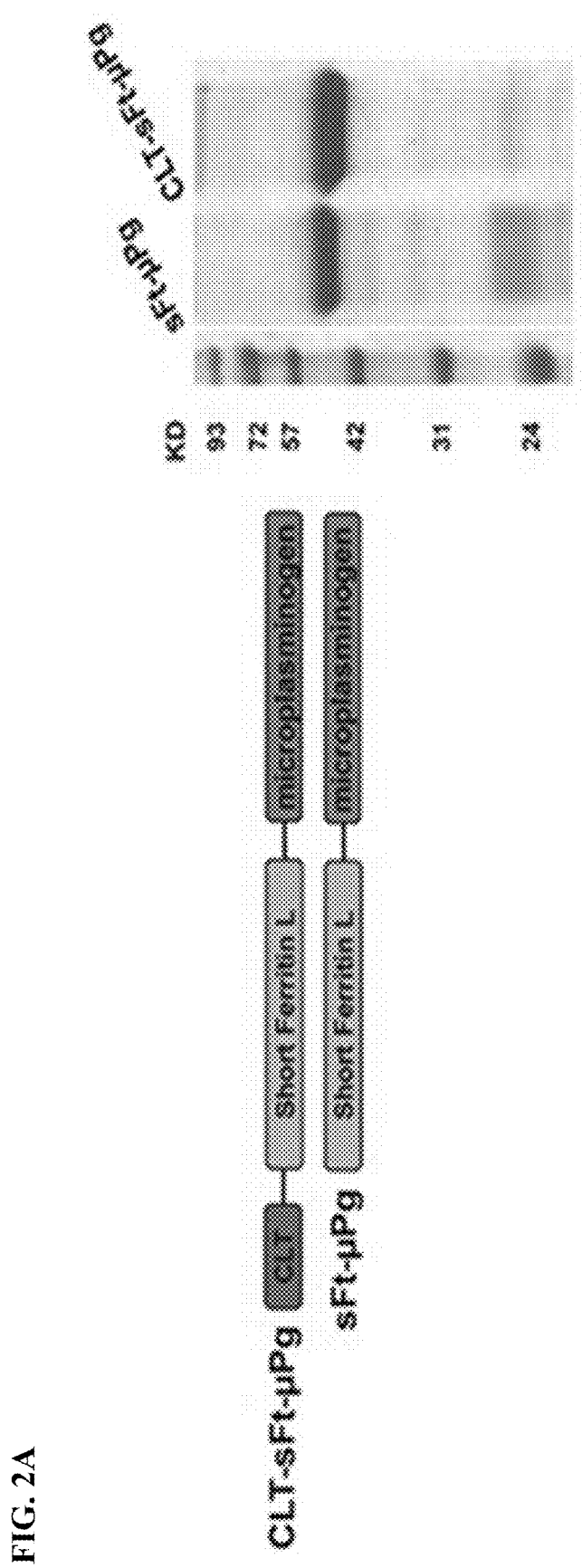

FIG. 2A shows schematic diagrams of CLT-sFt-μPg and sFt-μPg, and shows SDS-PAGE results of the purified cages.

Figure 2B:
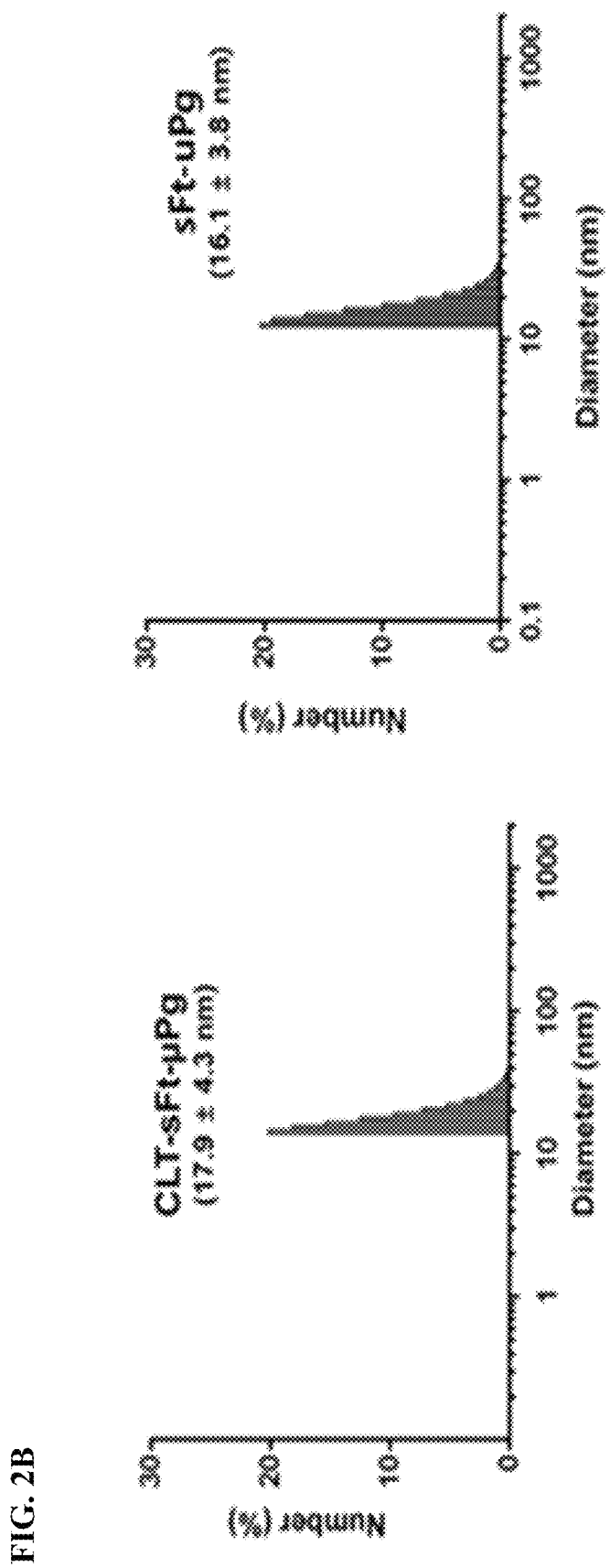

FIG. 2B shows DLS analysis results of CLT-sFt-μPg DCNC and sFt-μPg DCNC.

Figure 2C:
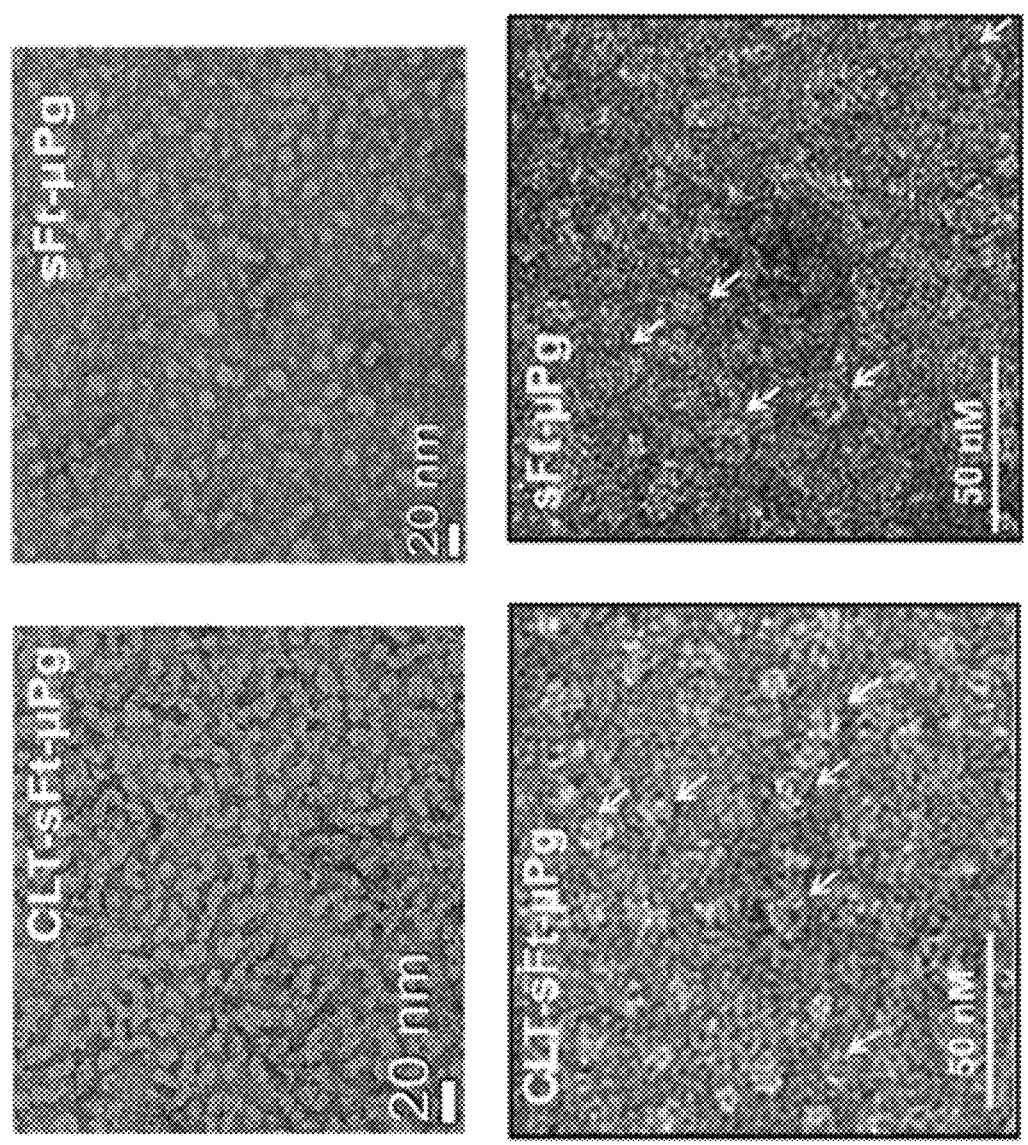

FIG. 2c shows transmission electron micrographic (TEM) analysis results of CLT-sFt-μPg DCNC and sFt-μPg DCNC.

Figure 3A:
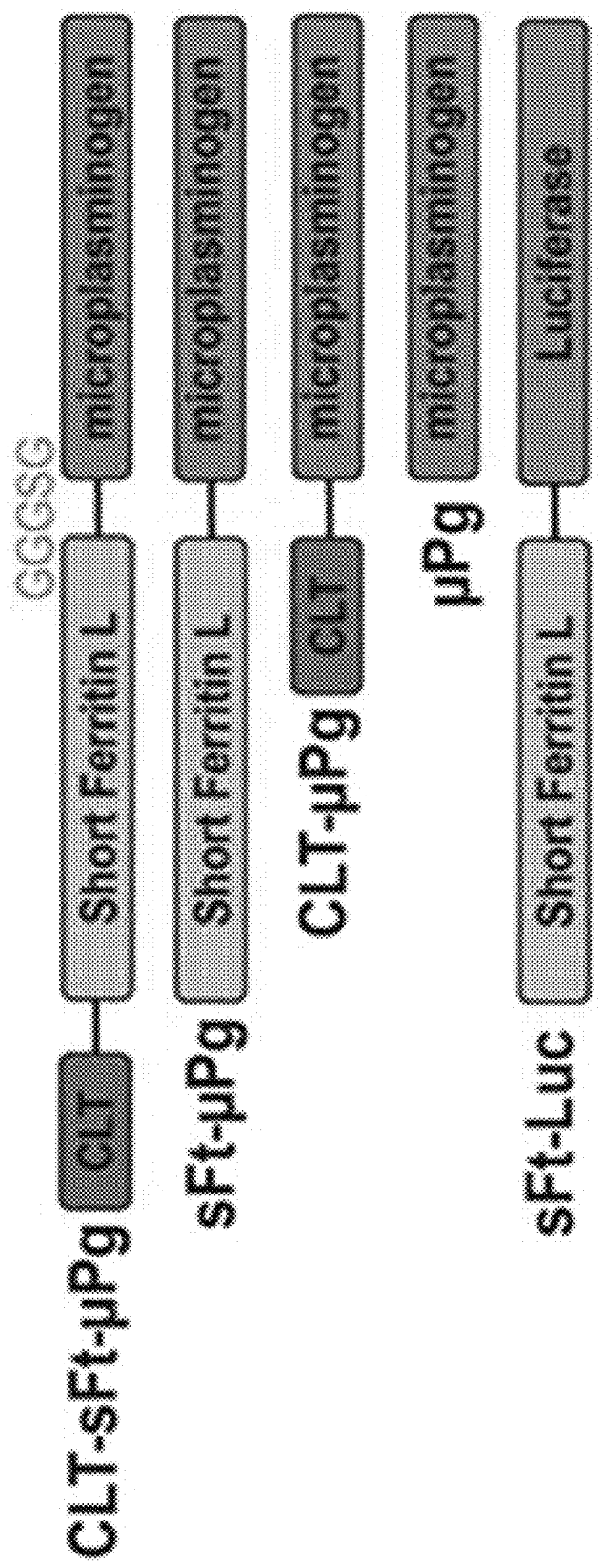

FIG. 3A shows schematic diagrams of the proteins used in the present invention. The flexible linker (GGGSG) is inserted between ferritin fragment and microplasminogen.

Figure 3B:
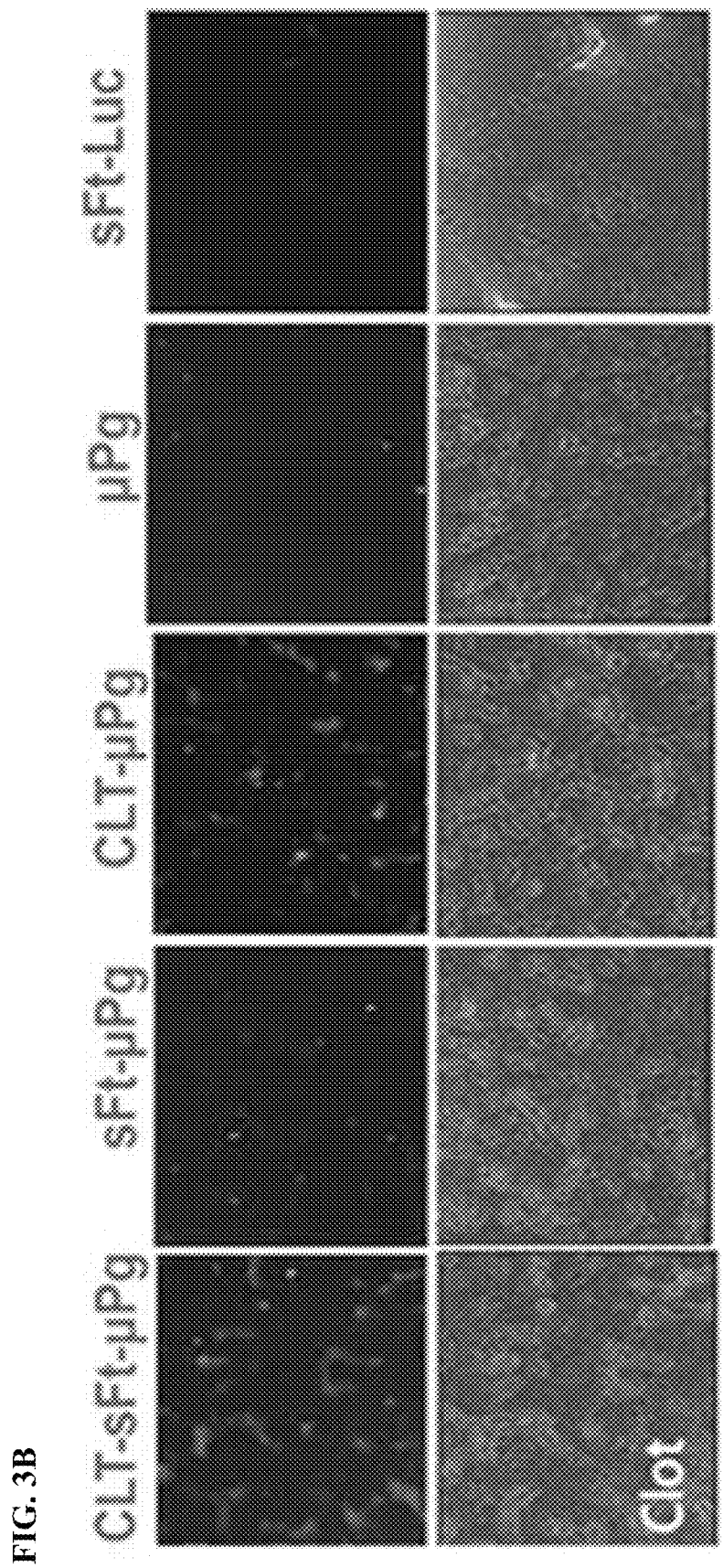

FIG. 3B shows the results, wherein after the formation of clots, the FITC-labeled proteins were added on the clots at a concentration of 1.25 μM to monitor through a fluorescence microscope whether the proteins were bound to the clots. The clots were visualized under an optical microscope.

Figure 3C:
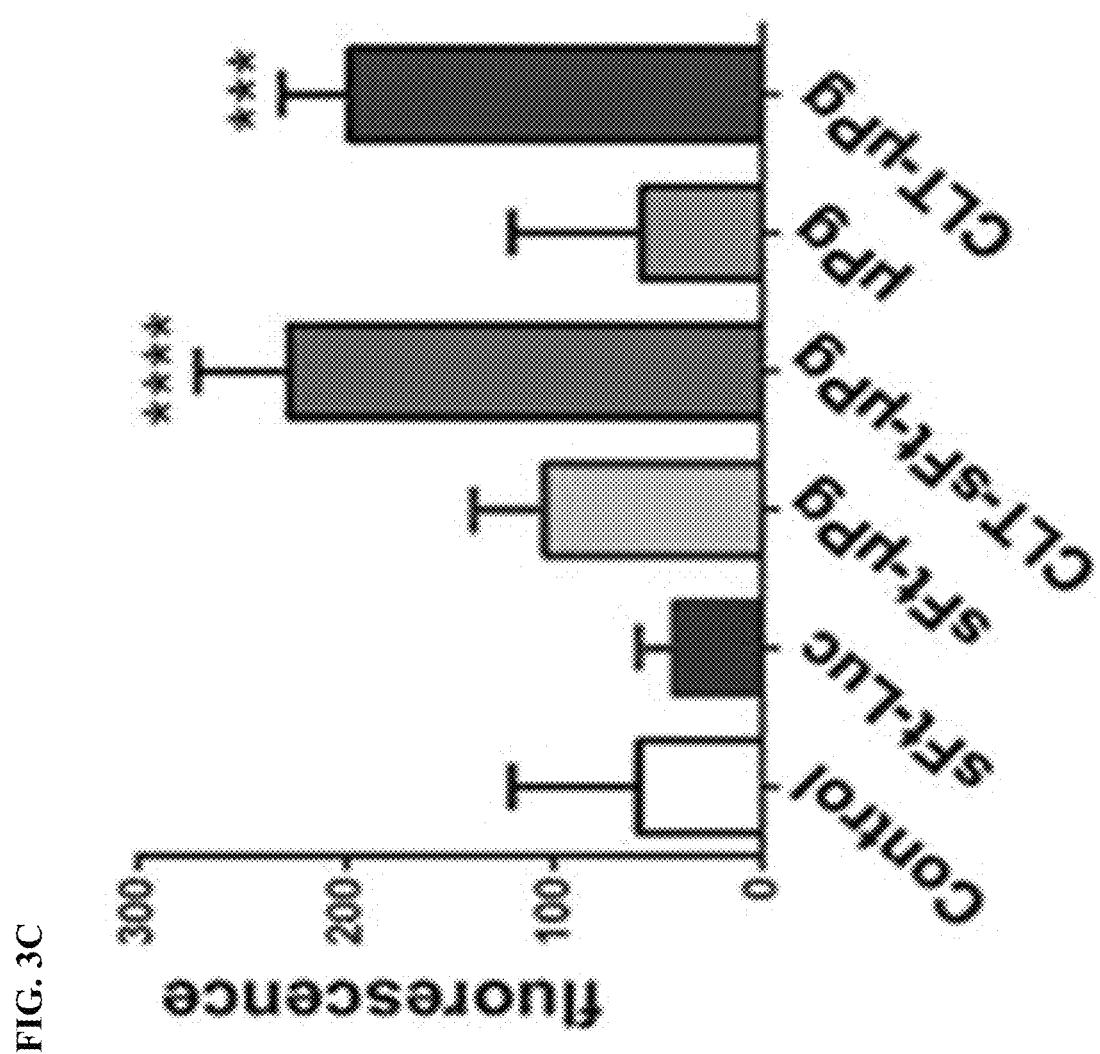

FIG. 3C shows the results, wherein the FITC-labeled proteins (1 μM) were added to clots and then the amounts of bound proteins were quantified using a fluorescence spectrometer (ANOVA test, **: P<0.0001, *: P=0.0003).

Figure 3D:
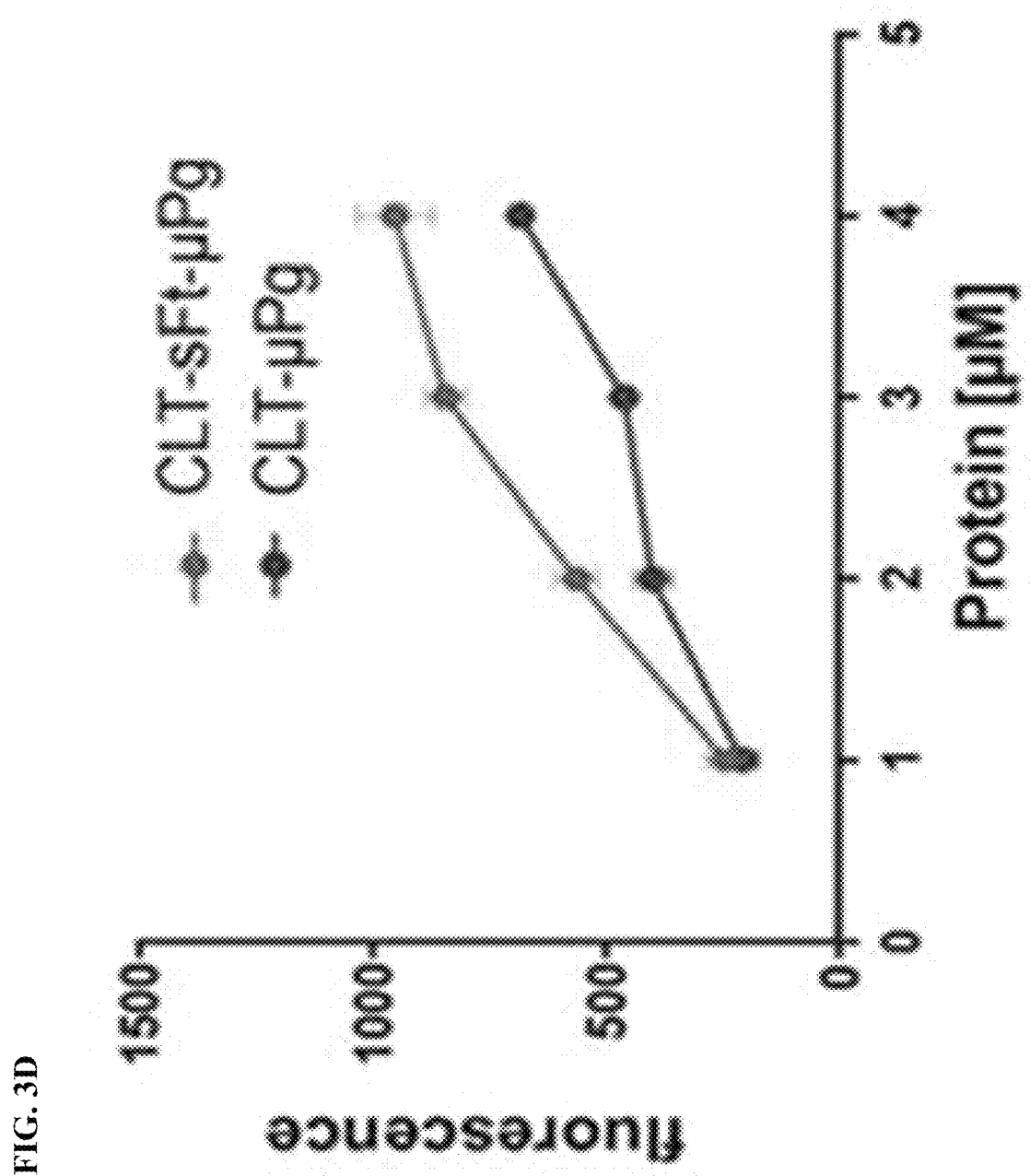

FIG. 3D shows the results, wherein CLT-sFt-μPg and sFt-μPg (1-4 μM) were added on clots and then the amounts of proteins bound to the clots were quantified.

Figure 4A:
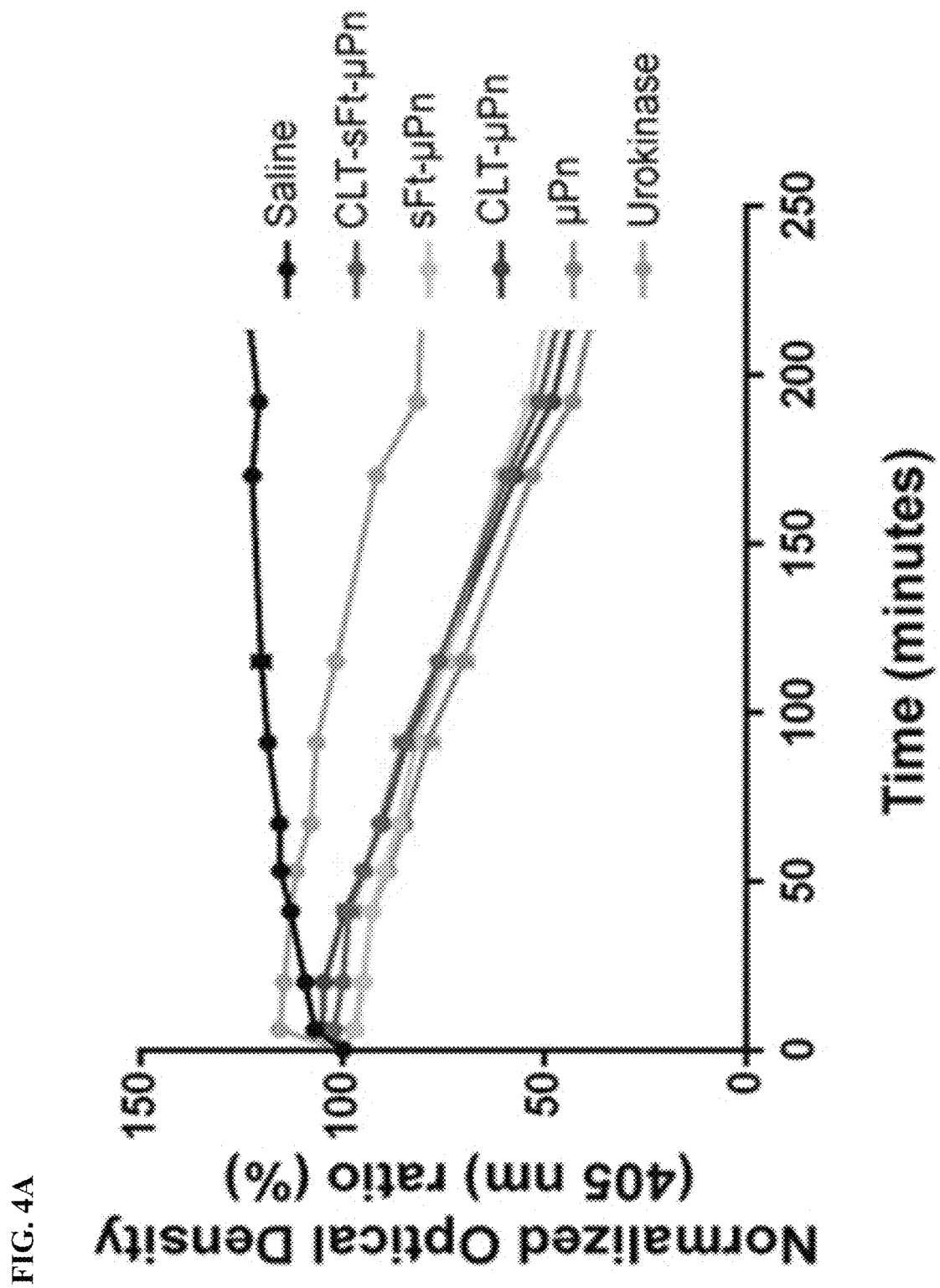

FIG. 4A shows the results of evaluating the degree of clot dissolution through turbidity, wherein the clots in 96-well plates were incubated with each of the proteins (7 μM) during the indicated times and then the absorbance was measured at 405 nm.

Figure 4B:
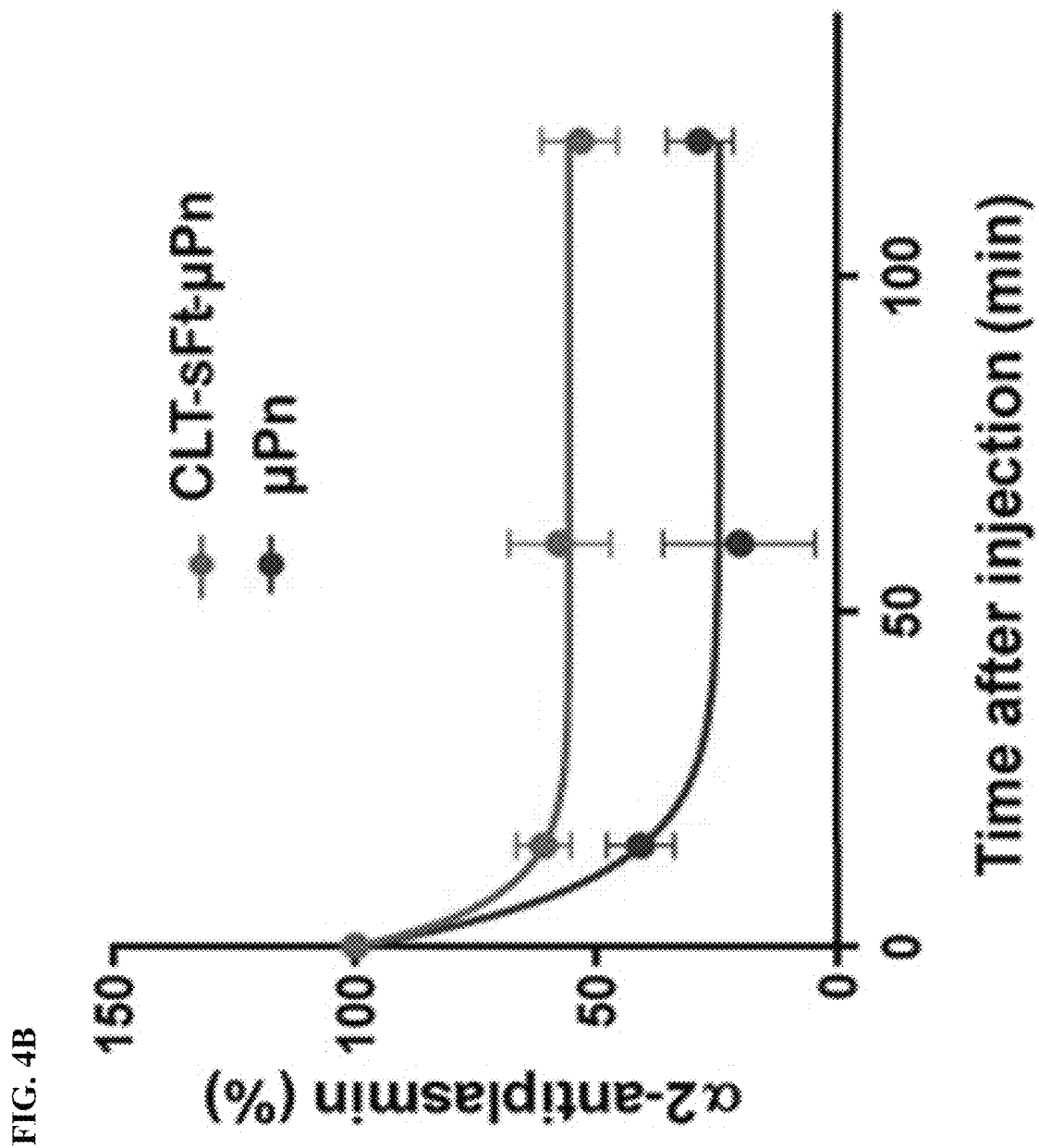

FIG. 4B shows the results, wherein CLT-sFt-μPn or μPn was intravenously administered into mice and then the amount of α2-anti-plasmin in blood was measured.

Figure 4C:
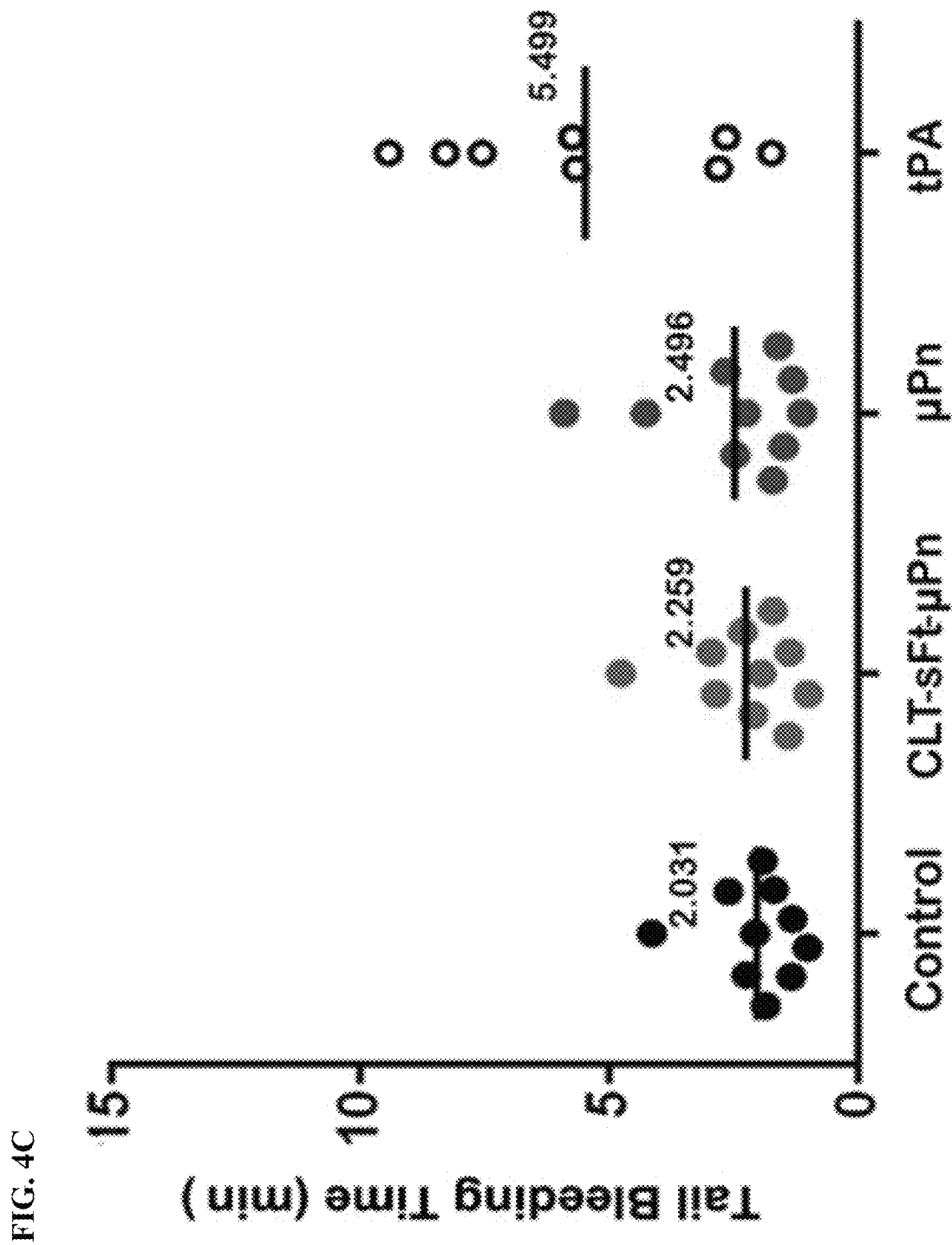

FIG. 4C shows the results, wherein CLT-sFt-μPn or μPn was intravenously administered into mice and then the time to stop bleeding on the wound of mouse tail ends was measured.

Figure 5A:
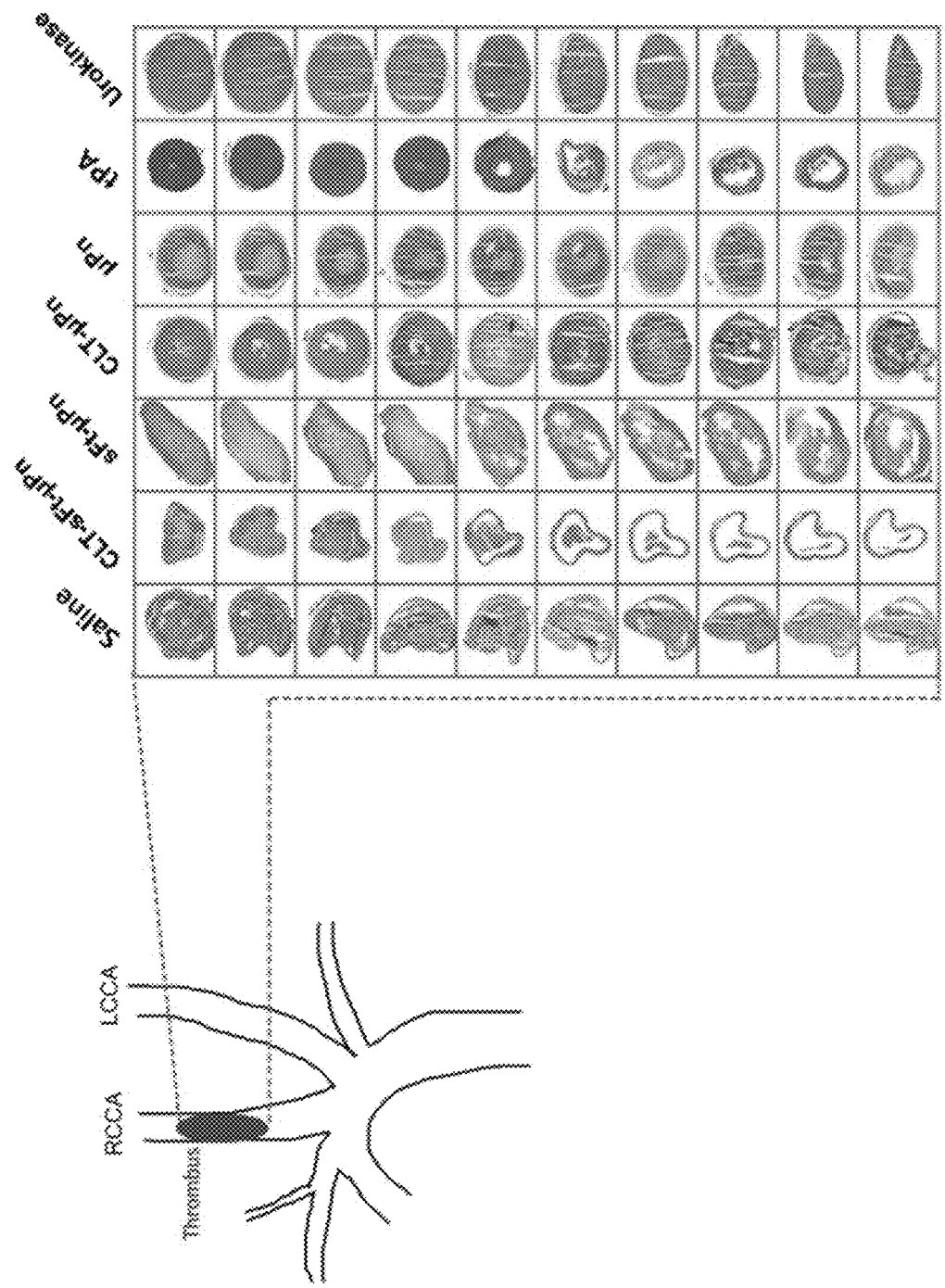

FIG. 5A shows the results, wherein when respective proteins were treated following the blood occlusion by the induction of thrombosis in right central carotid artery of mice, the 12 transverse sections of the blood vessel were observed through H/E staining to investigate the degree of clot dissolution (RCCA: right central carotid artery).

Figure 5B:
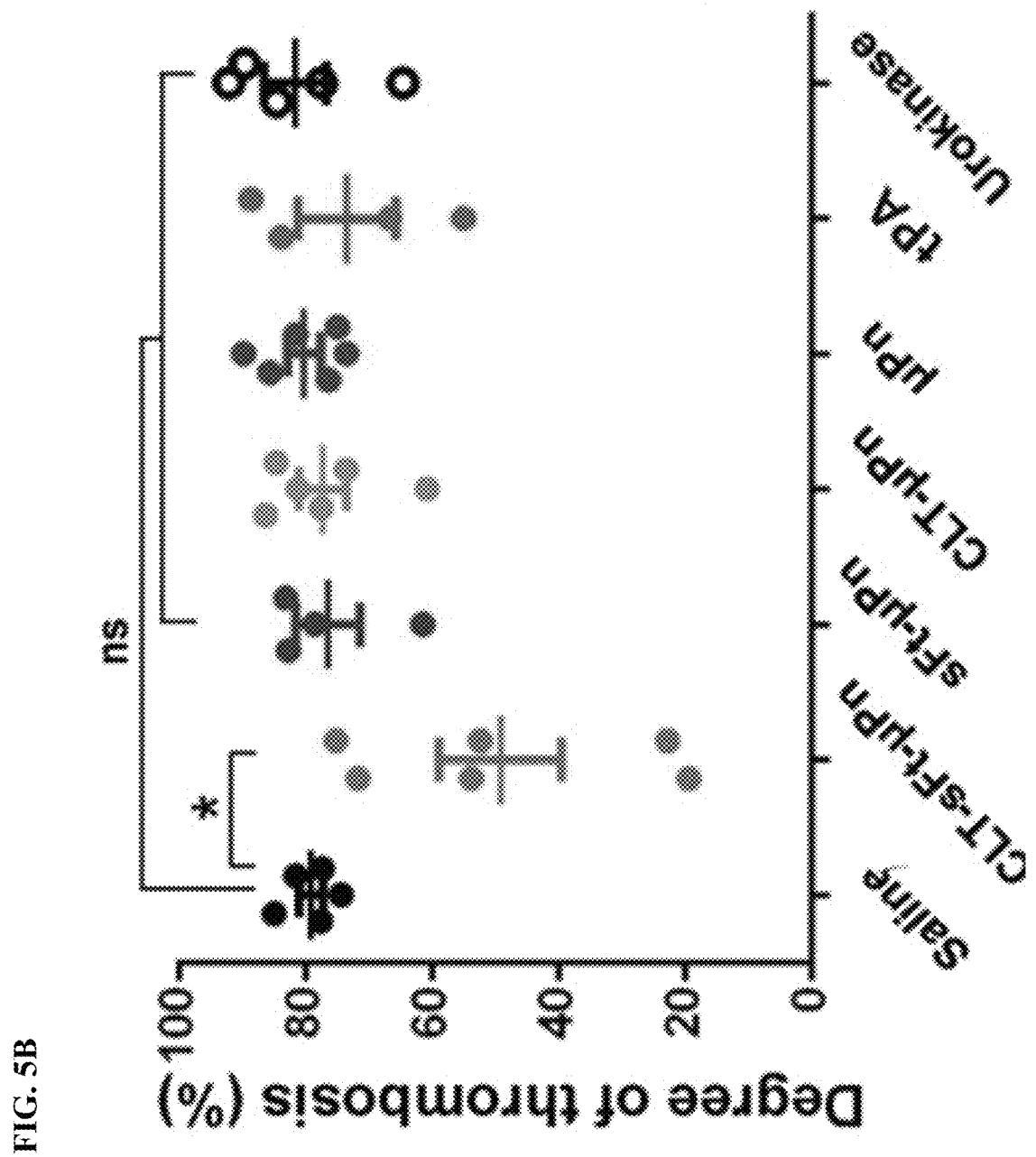

FIG. 5B shows the results, wherein the degree of occlusion of the blood vessel by clots was measured by the inForm program (PerkinElmer) and the area occupied by clots in each section relative to the overall vessel section area was quantified and normalized.

Figure 5C:
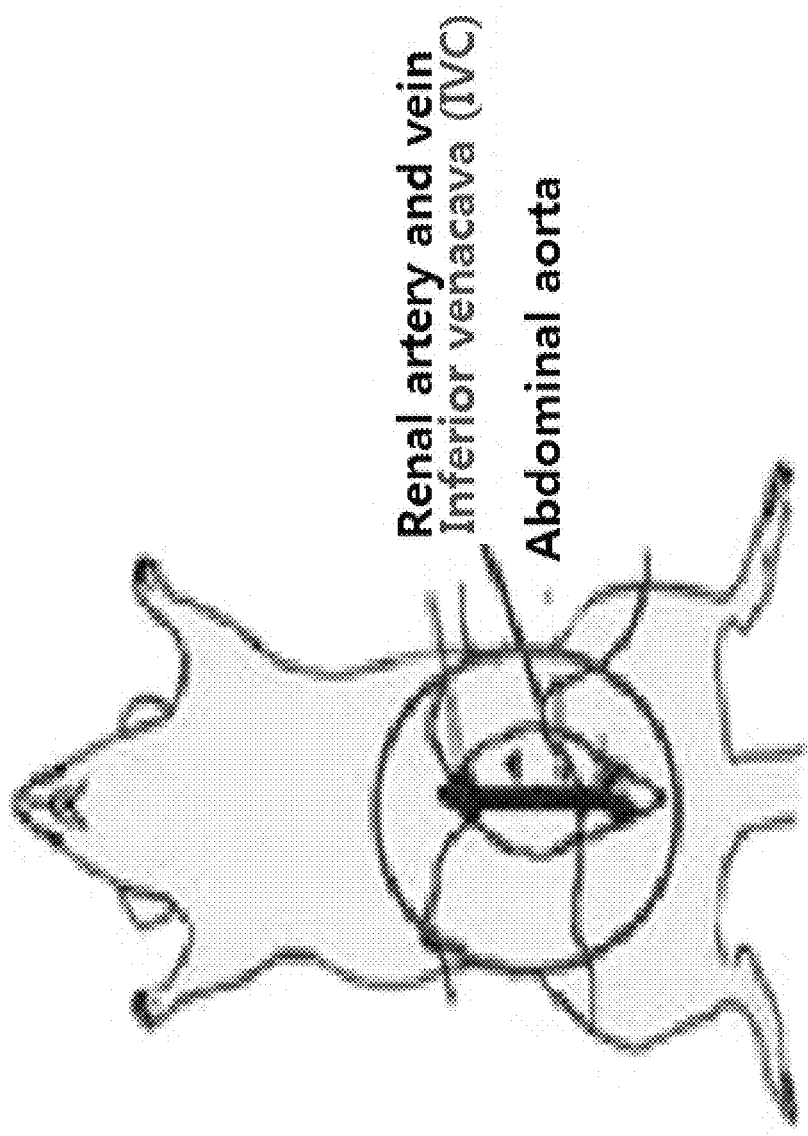

FIG. 5C shows a diagram of a deep vein thrombosis animal model.

Figure 5D:
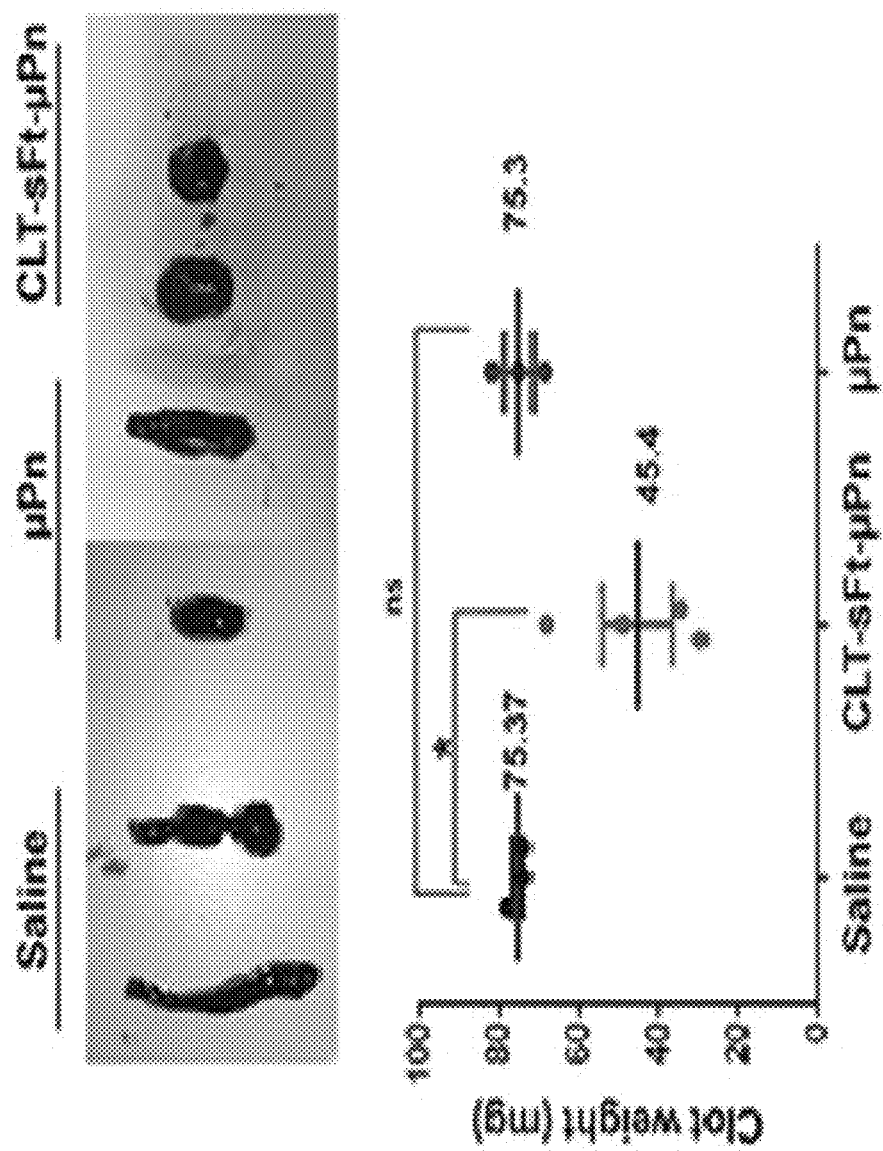

FIG. 5D shows the results of naked-eye observation of clots remaining after treatment with each protein (top) and the results of measurement of each clot weight (bottom).

MODE FOR CARRYING OUT THE INVENTION

Hereinafter, the present invention will be described in detail.

However, the following examples are merely for illustrating the present invention and are not intended to limit the scope of the present invention.

<Methods>

1. Construction of Clot-Targeting Peptide (CLT)/Microplasminogen-Conjugated Double Chambered Nanocages and CLT-Microplasminogen Fusion Proteins The recombinant plasmids for expressing the double chambered nanocage (DCNC) and control protein were constructed using modified pET28 vector (Novagen). The modified pET28 contains extra cleavage sites of KpnI and NheI between NcoI/NdeI and an extra cleavage site of SpeI between SalI/XhoI. The gene encoding the short ferritin light chain (sFt) was prepared through PCT from cDNA of the human ferritin light chain, and as previously reported (ACS nano 7, 7462-7471, 2013), was incorporated between Nde1 and BamH1 for the expression in $E.$ $coli$. The CLT protein (CNAGESSKNC)-encoding oligonucleotide was synthesized and then inserted between KpnI and NheI. The microplasminogen (μPg) was prepared through PCR, and inserted between Spe1 and XhoI. The flexible linker (GGGSG) was synthesized, and then inserted between SalI and SpeI, and finally the linker (GSEFVDGGGSGTA) was produced between the μPg and ferritin in the CLT-sFt-μPg structure. The sFt-μPg was constructed using the same method as above except for the insertion of the CLT peptide. The free μPg (free μPg) and the CLT-conjugated μPg were constructed using the same vector and restriction sites as above.

2. Characterization of CLT-sFt-μPg Double Chambered Nanocages (DCNCs)

After expression and purification of proteins, the double chambered nanocage (DCNC) proteins (CLT-sFt-μPg and sFt-μPg) were analyzed using the dynamic light scattering (DLS) instrument (ELS-Z, Otzuka Electronics, Japan). The shape and size of the double chambered nanocages were observed using transmission electron microscopy (TEM).

Each sample was diluted to 0.2 mg/mL, and applied to CF-200-Cu grids (Electron Microscopy Sciences), and washed three times. Thereafter, the sample was negatively stained with 2% uranyl acetate, and images were acquired using TEI Tecnai at the Korea Institute of Science and Technology.

3. Structure Modeling of CLT-sFt-μPg DCNC

The structure of CLT-sFt-μPg single unit was modeled using MODELLER v9.12 on the basis of the crystal structures of human ferritin (PDB 2FG4) and microplasminogen (PDB 1QRZ). A total of 1,000 monomeric structures were produced, and assembled into CLT-sFt-μPg DCNC based on the wild-type ferritin cage structure (PDB 3A68) using PyMOL. At least 20 structures deviating from the standard were re-established using GROMACS, and a structure that showed no deviation from the standard and the lowest energy was selected as a model.

4. Clot Binding Analysis

Clots were formed by adding $CaCl_2$ (10 mM) and thrombin (0.5 U/mL) to fresh frozen plasma (FFP, 0.2 mL) and standing the mixture at 37° C. for 1 hour, and washed thoroughly using PBS. FITC-labeled proteins (1-4 μM) were added to on the clots, followed by incubation at 37° C. for 30 minutes. Thereafter, washing for removing the unbound substances was carried out. The fluorescence was monitored at an excitation wavelength of 488 nm and an emission wavelength of 520 nm using the SPECTA MAX BEMINI EM (MOLECULAR DEVIDES). For microscopic observation, the thin-layered clots were placed on the 1 mm-thick glass plates, and each protein was incubated at a concentration of 1.25 μM, washed with PBS, and observed under a fluorescence microscope. To verify that the activity of the peptides linked to both termini of the short ferritin fragment is not affected by the formation of the cage, equivalent molar concentrations of ferritin monomer and free protein were also incubated.

5. Clot Lysis Ability (Turbidity) Analysis

The analysis was performed at room temperature in costar 96-well EIA/RIA plates (in triplicate) using the SUNRISE-BASIC reader (TECAN, Switzerland). Clots were generated by the same method as described above. For dissolution of the formed clots, each protein (7 μM) was added to the clots. Before clot dissolution, the microplasminogen or microplasminogen-fused peptides were activated by urokinase at 37° C. for 1 hour. Therefore, clot lysis was performed in the presence of urokinase.

6. Analysis of α2-Anti-Plasmin in Plasma and Investigation of Bleeding Side Effects Levels of α2-anti-plasmin in rodent were analyzed according to the previous reported method (Blood 97, 3086-3092, 2001). The activated CLT-sFt-μPn (7.9 mg/kg) and μPn (5 mg/kg) proteins were injected into via tail veins of ICR mice (6-8 week old: 18-26 g) (μPn: microplasmin). The same volume of saline was injected for control. 20 μL of animal blood was collected at the predetermined times (15 minutes, 60 minutes, and 120 minutes), and the plasma was prepared. To analyze the levels of α2-anti-plasmin, in vitro plasmin activity was measured before and after the mixing with rodent plasma.

10 μL of plasma was diluted using 420 μL of 0.05 M Tris-HCl buffer (pH 7.4), 100 mM NaCl, and 0.01% Tween 20, and 5 nM plasmin was added. After incubation for 10 seconds, 50 μL of 3 mM S2403 (Chromogenics, Antwerp, Belgium) was added to reaction samples, and the absorbance changes were measured at 405 nm. The absorbance changes were about 0.18 per minute in the buffer alone treatment group (i.e., 0% α2-anti-plasmin) and about 0.09 per minute in the plasma of the animals treated with saline (i.e., 100% α2-anti-plasmin). Calibration curves were made on the basis of the above results.

In addition, after wounds were created in tail ends of ICR mice (6-8 week old: 18-26 g) administered with the activated CLT-sFt-μPn (7.9 mg/kg) and μPn (5 mg/kg) proteins, the time to stop bleeding was measured. Same volumes of saline and tPA were administered for control.

7. Arterial Thrombosis Model

Male ICR (6-8 week old, 18-25 g) were housed in a pathogen-free environment with a temperature and humidity maintained. The mice were anesthetized, and the skin was incised to expose the right common carotid artery. The fascia was directly incised, and the right common carotid artery was partially exposed. Clots were induced by inserting a piece of filter paper sufficiently wet with $FeCl_3$ (5%) under the right common carotid artery, and the inserted filter paper was removed after 3 minutes.

Two minutes after occlusion by clot formation, 100 μL of 64.25 μM CLT-sFt-μPn, μPn, and CLT-μPn were injected via tail vein. The injected proteins were activated by incubation with urokinase for 1 hour (1:20), and the same amount of urokinase was independently injected as control. The carotid arteries of mice were perfusion fixed, stained hematoxylin and eosin (H/E), and retrieved for histological analysis. Twelve transversal histology sections of injured carotid arteries were evenly cut and subjected to H/E staining, and observed under VECTRA 3.0 (Perkinelmer).

The occluded area was measured by inForm program (Perkinelmer), and normalized in % in relation to the total vessel lumen to quantify the degree of thrombosis of each section. The average of twelve sections for each mouse treated with each protein was floated.

8. Deep Vein Thrombosis Model

Vein thrombosis animal models were prepared as reported in the prior art document (Thrombisis and haemostasis 105, 1060-1071, 2011). Briefly, SD rats were anesthetized, and the superior vena cava and the inferior vena cava were exposed to be segregated from other adjacent organs. Each end (3 cm) of the vena cava was loosely tied with 2-0 silk thread, and branched vessels were tightly ligated. Immediately, 20 UI of thrombin was injected through the tail vein.

Thirty minutes after occlusion by clot formation, CLT-sFt-µPn (7.92 mg/kg) or µPn (5 mg/kg) was intravenously injected though the via tail vein. Each of the injected proteins was pre-activated by incubation with urokinase for 1 hour, and a same amount of urokinase was independently injected as control. After 60 minutes, the veins were segregated and stored in a Petri dish containing PBS. The thrombolytic activity was evaluated by immediately measuring the wet weight of the clots.

<Results>

1. Manufacturing of Cage Nanoparticles of Fusion Protein and Characterization Thereof To develop a microplasmin-based thrombolytic agent, the present inventors designed a double-chambered nanocage (DCNC). As shown in FIG. 1A, multivalent clot-targeting (CLT) peptides and microplasmin proteins coexist on the surface of DCNC.

The ferritin forms a nanoparticle, such as a cage, and various functional fractions may be chemically or genetically conjugated onto such a cage. The idea regarding the use of DCNC is that the peptide and protein payloads can offer double activities. These activities are augmented by binding activity of the ligands and do not impede each other's function.

The CLT (CNAGESSKNC) peptide used in the present invention was identified by phage display that can recognize fibrin-fibronectin complexes in clots. The present inventors used a short fragment (sFt) of the human ferritin light chain, and produced such a short fragment by removing the fifth helix of the wild-type ferritin. The peptides and proteins loaded in the cage formed by short ferritin monomers did not impede each other's binding activity and physiological activity.

The microplasminogen (µPg) can be activated into microplasmin (µPn) by the cleavage of Arg-Val residues through urokinase. The activated microplasmin is a two-chain disulfide-linked serine protease, and is homologous to trypsin with the classic catalytic triad of His, Asp, and Ser.

The microplasmin is converted from microplasminogen by a plasmin activation enzyme, such as tPA or UPA, and has fibrin cleaving/dissolving activity. UPA cleaves between Arg580 and Val581 of the microplasminogen to convert to the microplasminogen into microplasmin including Val581 to the end residue. Since the stability of the microplasmin is lowered at the neutral pH, the proteins are produced and purified in a form of microplasminogen, and then activated by UPA before use in the present experiments.

To predict orientations and display patterns of CLT peptides and microplasminogen protein payloads, a structure model of CLT-sFt-µPg sub unit was built by homologous modeling with MODELLER v9.12 (FIG. 1A). As shown in FIG. 1A, four copies of microplasminogen, each of which is fused to the C-terminus of sFt, are assembled into 4-fold symmetry and show a petal-like appearance, and six petals are dispersed on the surface of the nanocage. Twenty four CLT peptides, each of which is linked to the N-terminus of sFt, are exposed toward to the outside of the nanocage (FIG. 1B). The microplasminogen payloads are oriented in a direction that can retain the activation cleavage site (Arg-Val), and the catalytic triad amino acid residues remained outside of the nanocage and accessible thereto (FIG. 1A).

The CLT-sFt-µPg and sFt-µPg DCNCs were purified, and differential light scattering (DLS) was performed to understand characteristics thereof (FIGS. 2A and 2B). The two types of DCNCs showed average sizes of 17.9 nm and 16.1 nm, respectively, which were similar to the predicted size from the prediction model. In other words, the results indicate that the modification for fusing the two peptides (CLT and microplasminogen) does not affect the overall cage characteristics.

2. Evaluation of Thrombolytic Ability of Fusion Peptide Nanocage

To assess the efficacy of CLT-sFt-µPg DCNC as a thrombolytic agent, (i) the clot-binding ability of the CLT peptide, (ii) the thrombolytic ability of microplasminogen and microplasmin, and (iii) the systemic inactivation of anti-plasmin were evaluated.

To evaluate these, the present inventors constructed µPg, CLT-conjugated microplasminogen (CLT-µPg) fusion protein, and luciferase-conjugated sFt(sFt-Luc) nanocages as controls (FIG. 3A). Clots, formed by the addition of $CaCl_2$) and thrombin to fresh frozen plasma (FFP), were incubated with proteins labeled with fluorescent groups, followed by washing to remove the unbound fluorescent substance.

For microscopic observation, thin-layered clots were formed on glass plates and the bound proteins were monitored. The CLT-conjugated products, i.e., CLT-sFt-µPg DCNC and CLT-µPg fusion protein were co-distributed with clots (FIG. 3B).

The present inventors used equivalent molar concentrations of ferritin monomers and glass proteins to verify that the activities of the cage payloads (CLT and microplasminogen) were not affected by the formation of the cage. The binding ability of each construct was quantified by incubating the fluorescence-labeled nanocages and proteins with clots in 96-well plates.

As a result, the binding ability of CLT-sFt-µPg DCNC was significantly higher than that of the CLT-µPg fusion protein, implying that the CLT peptides target clots with enhanced affinity due to the enhanced binding activity by the cage structure (FIGS. 3C and 3D).

The CLT-sFt-µPg DCNC, µPg, CLT-µPg protein, and sFt-µPg were activated using urokinase, and then incubated with clots in 96-well plates. As shown in clot turbidity analysis results in FIG. 4A, the activated µPn loaded in the cage or the free form of µPn effectively dissolved the clots and showed higher activity compared with urokinase alone (FIG. 4A). The slight increase of turbidity in the saline group was due to the slow formation of clots during the incubation time.

These results suggested that the µPn loaded in the cage or free form of µPn effectively dissolve clots. As for in vitro experiment, when the µPn loaded in the cage or free form of µPn were directly incubated with clots, CLT did not affect the lytic activity thereof. However, it could be confirmed through the following results that the clot-targeting ability by CLT is essential and very important in clot dissolution in vivo.

3. Confirmation of Stabilization Effect of Microplasmin by Nanocage and Bleeding Side Effects The present inventors investigated by monitoring the level of circulating α2-anti-plasmin whether the cage protein structure can shield the activated µPn from being degraded by anti-plasmin in the blood. It has been reported that intravenous plasmin or microplasmin are degraded respectively, to reduce the level of α2-anti-plasmin in the body. Therefore, the reduced level of α2-anti-plasmin in the body indicates the degradation of plasmin or microplasmin.

In addition, the tPA used in the clinic may cause systemic somatic hemorrhage. Therefore, to investigate whether the microplasmin loaded in the cage has bleeding side effects, wounds were created in tail ends of mice, and then the time to stop bleeding was measured.

As shown in FIG. 4B, the level of circulating α2-anti-plasmin decreased more slowly following intravenous administration of the activated CLT-sFt-μPn DCNC, compared with the administration of free form of μPn. This means that the nanocage structure shielded the μPn loaded in the cage from being degraded by anti-plasmin.

As shown in FIG. 4C, the times to stop bleeding in the mice treated with CLT-sFt-μPn and μPn were similar to that in saline control, but the time to stop bleeding was prolonged in the mice treated with tPA. It was therefore confirmed that tPA may cause bleeding side effects but CLT-sFt-μPn had no bleeding effects like μPn. Therefore, the fusion protein of the present invention can be advantageously used as a thrombolytic agent without side effects.

4. Evaluation of In Vivo Thrombolytic Activity

Arterial thrombi are different from venous thrombi with respect to causes, characteristics, and disease consequences. However, both types of thrombi may be life-threatening and thus need to be promptly removed.

To investigate the in vivo effect of the CLT-sFt-μPg DCNC as a thrombolytic agent, CLT-sFt-μPg DCNC and other control substances were intravenously administered in arterial thrombus mouse models.

As shown in FIG. 5A, as a result of observation of transverse histological sections of the right central carotid artery, the blood lump occluded the blood vessel when the blood vessel was exposed to 5% $FeCl_3$. As a result of administration of the activated CLT-sFt-μPn DCNC, the blood circulation was very improved, but the activated μPn, CLT-μPn, sFt-μPn, and urokinase alone failed to dissolve the blood clot or showed insufficient effects. Compared with effects of tPA, which is the thrombolytic agent currently used in clinics, the blood circulation improving effect of CLT-sFt-μPn was significantly excellent.

As shown in FIG. 5B, the injection of the activated CLT-sFt-μPn DCNC showed substantial thrombolytic/clot-bursting activity. The thrombolytic activity of the CLT-sFt-μPn DCNC was due to the accurate in vivo clot-targeting resulting from the presence of the CLT moiety. As shown in FIG. 3B, the targeting failure of CLT-μPn was determined to be due to the fact that free μPn lost activity thereof by anti-plasmin more easily than caged μPn. In addition, even when compared with tPA, the CLT-sFt-μPn had significantly excellent thrombolytic/clot-bursting activity.

As a result of observation of ex vivo images of right and left carotid arteries, the CLT-sFt-μPg DCNC very specifically targeted a clot area in the right central carotid artery. Contrast to the in vitro binding results, the CLT-μPg fusion protein did not show an effect of targeting clots in the right central carotid artery like free μPg. This may be the reason why the thrombolytic activity of the CLT-μPg fusion protein was low.

Next, the present inventors evaluated the activity of the CLT-sFt-μPg DCNC to dissolve thrombi in veins. An abnormal thrombus in a vein restricts the return of blood to the heart, and results in pain and swelling. Deep vein thrombosis is a type of thrombi that are formed in a major vein of the leg. When such a thrombus separates, circulates, and blocks the heart and lung blood vessels, it causes an acute pulmonary embolism.

As shown in FIG. 5C, the present inventors surgically block the inferior vena cava of the rat to form a prominent clot in the corresponding region. The rats treated with activated CLT-sFt-μPn DCNC developed smaller and lower-weight clots compared with the rats treated with saline or free μPn (FIG. 5D).

As set forth above, the CLT-sFt-μPn DCNC according to the present invention is a novel plasmin-based thrombolytic nanocage, and has an effect of targeting a thrombus site, low susceptibility to inhibitors present in the circulatory systems, and pharmaceutical activity to strongly destruct both arterial and venous thrombi.

INDUSTRIAL APPLICABILITY

The CLT-sFt-μPn DCNC according to the present invention is a novel plasmin-based thrombolytic nanocage, and has an effect of targeting a thrombus site, low susceptibility to inhibitors present in the circulatory systems, and pharmaceutical activity to strongly destruct both arterial and venous thrombi, and thus has superior industrial applicability.

The invention claimed is:

1. A fusion peptide, comprising:
   (a) a clot-targeting peptide defined by the amino acid sequence of SEQ ID NO: 1;
   (b) a peptide defined by the amino acid sequence of SEQ ID NO: 3; and
   (c) any one peptide selected from the group consisting of microplasminogen defined by the amino acid sequence of SEQ ID NO: 5, and microplasmin defined by the amino acid sequence of SEQ ID NO: 6,
   wherein the peptides (a), (b), and (c) are sequentially linked.

2. The fusion peptide of claim 1, wherein the clot-targeting peptide (a) is linked to the N-terminus of the peptide (b) and the peptide (c) is linked to the C-terminus of the peptide (b).

3. The fusion peptide of claim 1, wherein the clot-targeting peptide (a) or the peptide (c) is linked to the peptide (b) via a linker.

4. A fusion peptide comprising the amino acid sequence of SEQ ID NO: 7.

5. A cage protein consisting of the fusion peptide of claim 1.

6. A polynucleotide encoding the fusion polypeptide of claim 1.

7. An expression vector comprising the polynucleotide of claim 6.

8. A host cell transformed with the expression vector of claim 7.

9. A pharmaceutical composition for preventing or treating a thrombotic disease, the composition comprising the fusion peptide of claim 1 as an active ingredient.

10. The composition of claim 9, wherein the thrombotic disease is selected from the group consisting of acute myocardial infarction, ischemic stroke, hemorrhagic stroke, deep vein thrombosis, lower limb edema, acute peripheral arterial occlusion, deep vein thrombosis, portal vein thrombosis, acute renal vein occlusion, cerebral venous sinus thrombosis, angina pectoris, cerebral infarction, and central retinal vein occlusion.

11. A method for treating a thrombotic disease in a subject in need thereof, the method comprising administering the fusion peptide of claim 1 to the subject in an amount effective for treating the thrombotic disease.

12. The method of claim 11, wherein the thrombotic disease is selected from the group consisting of acute myocardial infarction, ischemic stroke, hemorrhagic stroke, deep vein thrombosis, lower limb edema, acute peripheral arterial occlusion, deep vein thrombosis, portal vein thrombosis, acute renal vein occlusion, cerebral venous sinus thrombosis, angina pectoris, cerebral infarction, and central retinal vein occlusion.

* * * * *